US009962216B2

(12) United States Patent
Takei

(10) Patent No.: US 9,962,216 B2
(45) Date of Patent: May 8, 2018

(54) TREATMENT DEVICE

(71) Applicant: OLYMPUS CORPORATION, Tokyo (JP)

(72) Inventor: Yusuke Takei, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/192,441

(22) Filed: Jun. 24, 2016

(65) Prior Publication Data

US 2016/0302845 A1    Oct. 20, 2016

Related U.S. Application Data

(63) Continuation of application No. PCT/JP2014/084362, filed on Dec. 25, 2014.
(Continued)

(51) Int. Cl.
*A61B 17/14* (2006.01)
*A61B 18/08* (2006.01)
(Continued)

(52) U.S. Cl.
CPC .. *A61B 18/085* (2013.01); *A61B 2017/00353* (2013.01); *A61B 2017/32004* (2013.01);
(Continued)

(58) Field of Classification Search
CPC ... A61B 17/28; A61B 17/2804; A61B 17/285; A61B 17/29; A61B 2017/2926;
(Continued)

(56) References Cited

U.S. PATENT DOCUMENTS 5,876,401 A * 3/1999 Schulze ........... A61B 17/07207
606/41
6,117,152 A * 9/2000 Huitema .......... A61B 17/00008
601/2
(Continued)

FOREIGN PATENT DOCUMENTS

JP    H08-275951 A    10/1996
JP    2001-170070 A    6/2001
(Continued)

OTHER PUBLICATIONS

Mar. 24, 2015 International Search Report issued in Patent Application No. PCT/JP2014/084362.
(Continued)

*Primary Examiner* — Anh Dang
*Assistant Examiner* — Erin Colello
(74) *Attorney, Agent, or Firm* — Oliff PLC

(57) ABSTRACT

A treatment device to treat a living tissue, includes: first and second holding portions; a rotary member including a working portion including an edge portion which is rotated around a central axis equal to or substantially parallel with the longitudinal axis, the rotary member capable of moving the edge portion from the first holding portion to the second holding portion; a first guide portion provided in the first holding portion and capable of guiding the edge portion toward the second holding portion through the holding surface of the first holding portion; and a second guide portion provided in the second holding portion, and capable of guiding the edge portion to the second holding portion through the holding surface of the first holding portion.

18 Claims, 17 Drawing Sheets

Related U.S. Application Data

(60) Provisional application No. 61/921,224, filed on Dec. 27, 2013.

(51) Int. Cl.
*A61B 17/00* (2006.01)
*A61B 17/32* (2006.01)
*A61B 18/00* (2006.01)

(52) U.S. Cl.
CPC ............... *A61B 2018/00101* (2013.01); *A61B 2018/00601* (2013.01)

(58) Field of Classification Search
CPC .......... A61B 2017/2946; A61B 17/295; A61B 17/32; A61B 17/320016; A61B 17/32002; A61B 2017/320052; A61B 2017/32004; A61B 17/320068; A61B 2017/320072; A61B 2017/320076; A61B 17/320092; A61B 2017/320096; A61B 17/32053; A61B 17/320758; A61B 2018/00595; A61B 2018/00607; A61B 2018/1452; A61B 2018/1455; A61B 2018/1457; A61B 2017/22024; A61B 18/085; A61B 2018/00101; A61B 2018/1442; A61B 18/12; A61B 2018/0225; A61B 18/0206; A61B 2018/00916; A61B 2018/00601; A61B 2018/00577; A61B 2018/00202; A61B 2018/00196; A61B 2018/0019; A61B 2018/00184; A61B 2018/00005; A61B 2017/00353; A61B 17/320783; A61B 2017/22025; A61B 2017/22004; A61B 17/2202; A61B 2017/320766; A61B 2017/2496; G01M 7/022

See application file for complete search history.

(56) References Cited

U.S. PATENT DOCUMENTS

| | | | | |
|---|---|---|---|---|
| 6,241,740 B1* | 6/2001 | Davis | ................ | A61B 17/1227 606/139 |
| 6,332,889 B1* | 12/2001 | Sancoff | ............. | A61B 17/0469 606/139 |
| 6,527,786 B1* | 3/2003 | Davis | ................ | A61B 17/1227 606/151 |
| 6,786,913 B1* | 9/2004 | Sancoff | ............. | A61B 17/0469 606/146 |
| 7,131,980 B1* | 11/2006 | Field | .................. | A61B 17/0482 606/146 |
| 9,526,502 B2* | 12/2016 | Regadas | ............. | A61B 17/1114 |
| 2002/0010480 A1* | 1/2002 | Sancoff | ...................... | A61F 2/08 606/148 |
| 2002/0062123 A1* | 5/2002 | McClurken | ............ | A61B 18/14 606/34 |
| 2003/0009195 A1* | 1/2003 | Field | .................. | A61B 17/0469 606/219 |
| 2003/0105476 A1* | 6/2003 | Sancoff | .............. | A61B 17/0469 606/139 |
| 2003/0216613 A1* | 11/2003 | Suzuki | .............. | A61B 17/0469 600/104 |
| 2004/0092967 A1* | 5/2004 | Sancoff | .............. | A61B 17/0469 606/148 |
| 2009/0048589 A1 | 2/2009 | Takashino et al. | | |
| 2009/0270852 A1* | 10/2009 | Takashino | ............ | A61B 18/085 606/27 |
| 2010/0185196 A1* | 7/2010 | Sakao | .................. | A61B 18/085 606/51 |
| 2011/0152900 A1* | 6/2011 | Regadas | ............. | A61B 17/1114 606/153 |
| 2011/0196404 A1 | 8/2011 | Dietz et al. | | |

FOREIGN PATENT DOCUMENTS

| | | |
|---|---|---|
| JP | 2002-017738 A | 1/2002 |
| JP | 2010-536398 A | 12/2010 |
| JP | 2013-519434 A | 5/2013 |
| WO | 2013/049734 A1 | 4/2013 |

OTHER PUBLICATIONS

Dec. 1, 2015 Office Action issued in Japanese Patent Application No. 2015-545576.
Mar. 1, 2016 Office Action issued in Japana Patent Application No. 2015-545576.
Jun. 28, 2016 International Preliminary Report on Patentability issued in Patent Application No. PCT/JP2014/084362.
Aug. 25, 2017 Extended European Search Report issued in European Patent Application No. 14874102.8.

\* cited by examiner

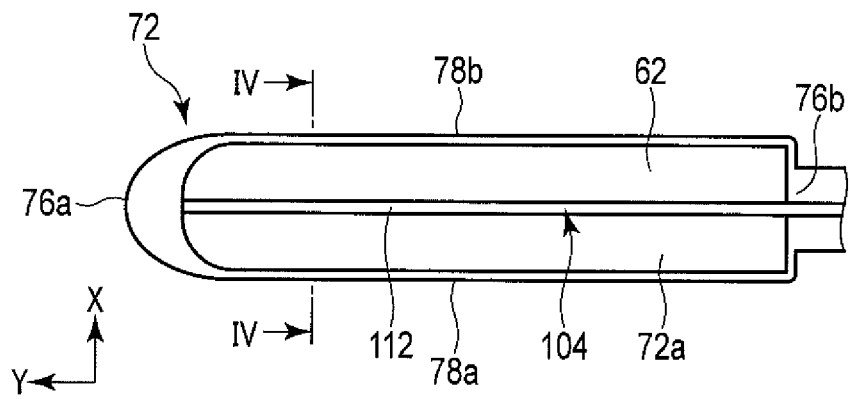
F I G. 3
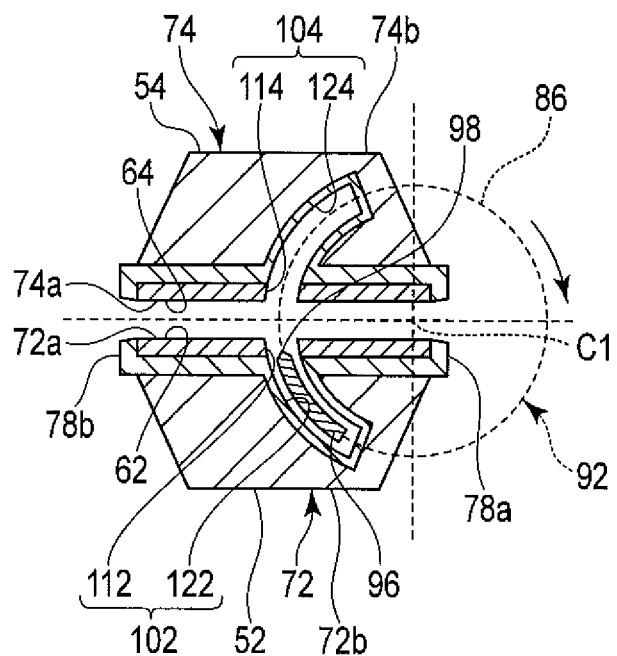
F I G. 4A

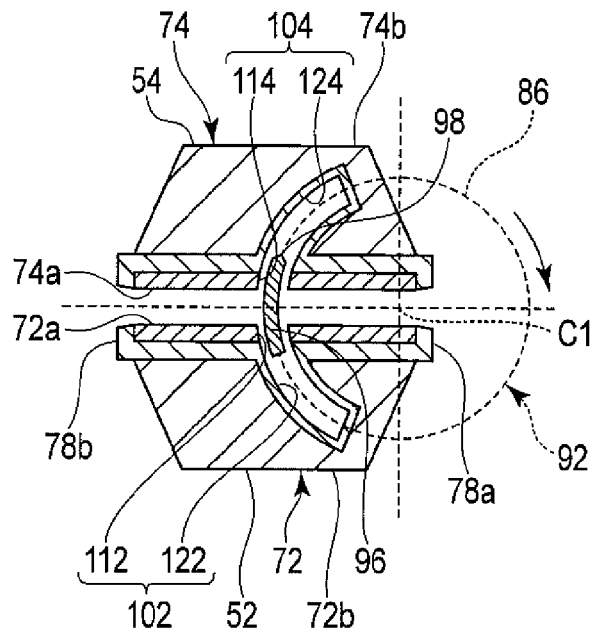
F I G. 4B
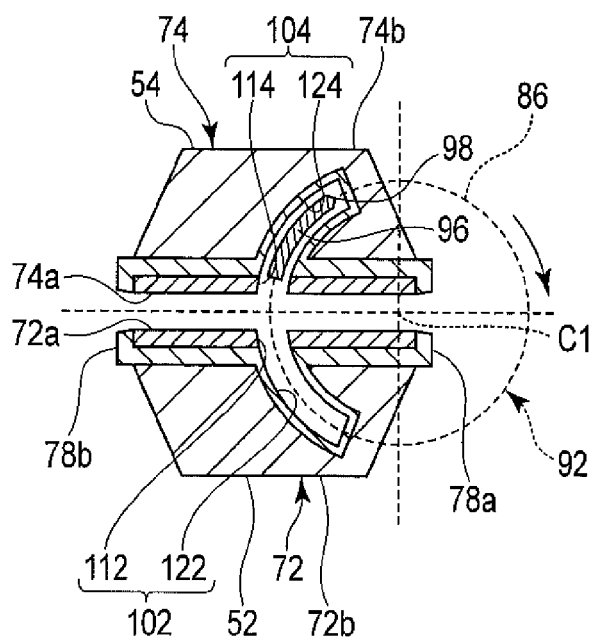
F I G. 4C

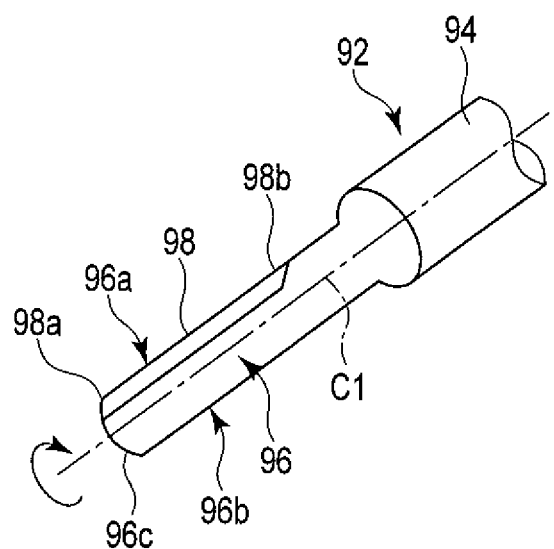
F I G. 5A
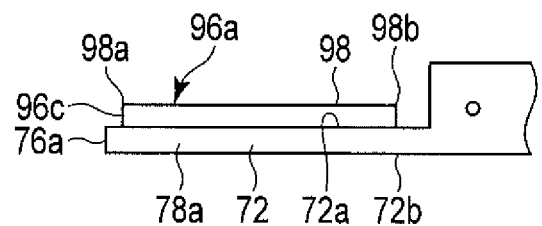
F I G. 5B

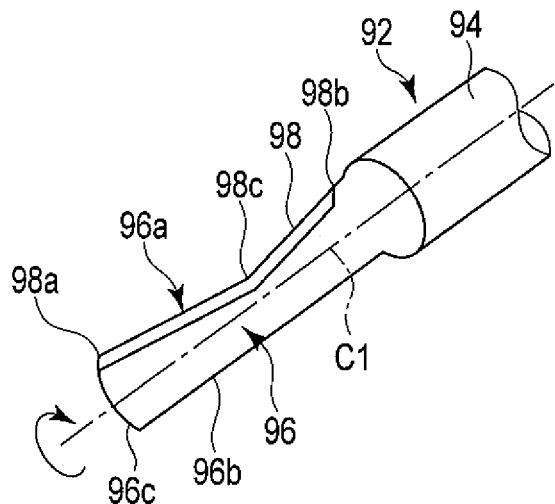
F I G. 8A
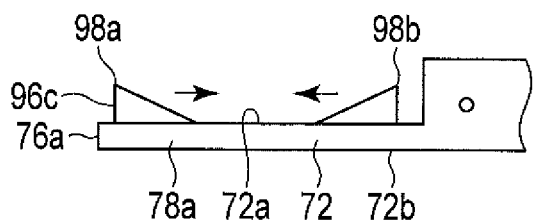
F I G. 8B

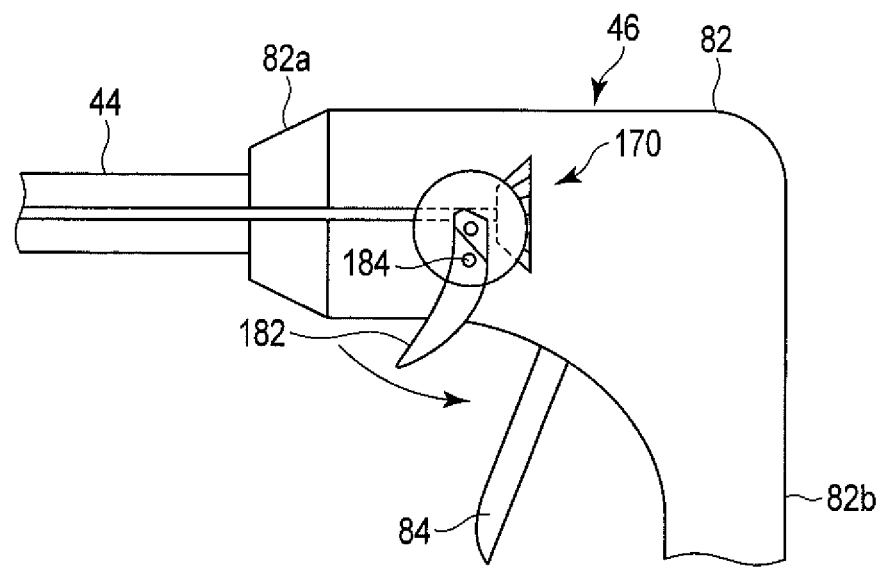
F I G. 11A
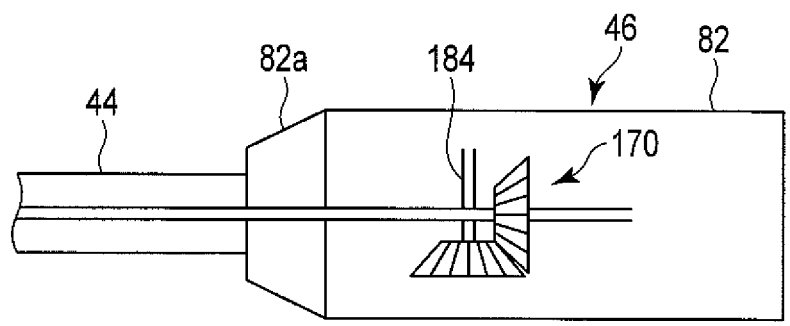
F I G. 11B

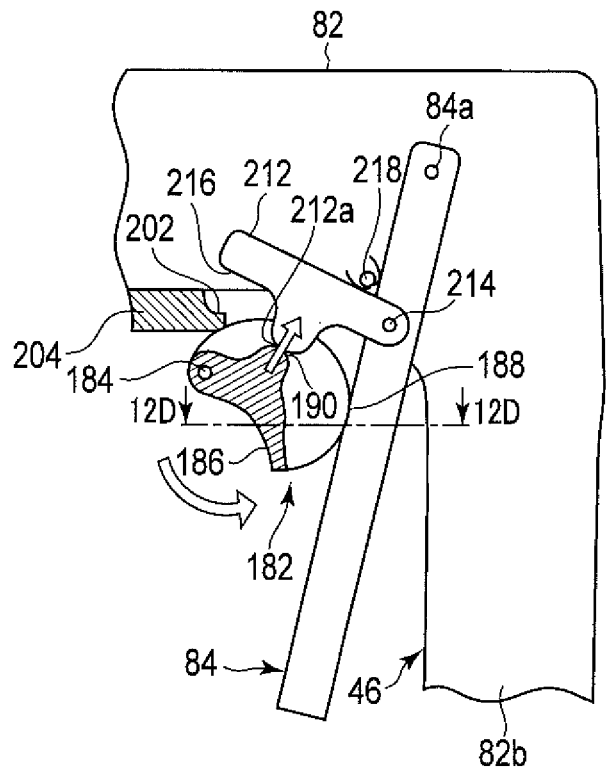
F I G. 12C
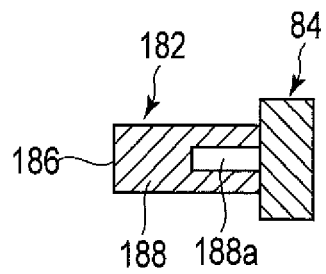
F I G. 12D

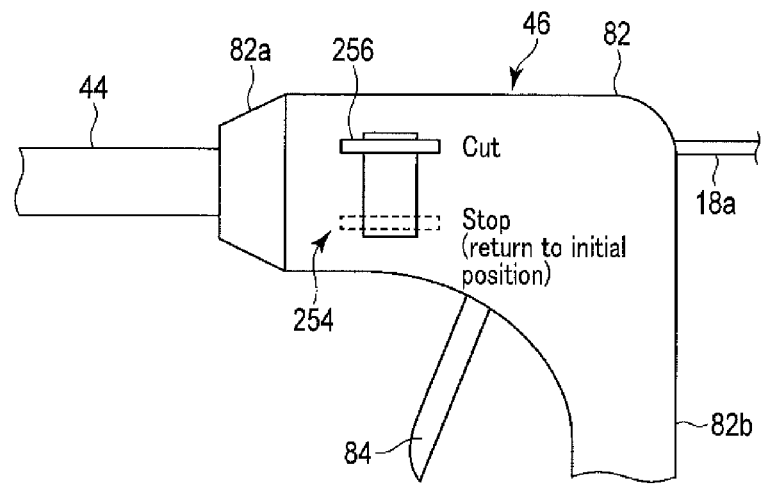
F I G. 13A
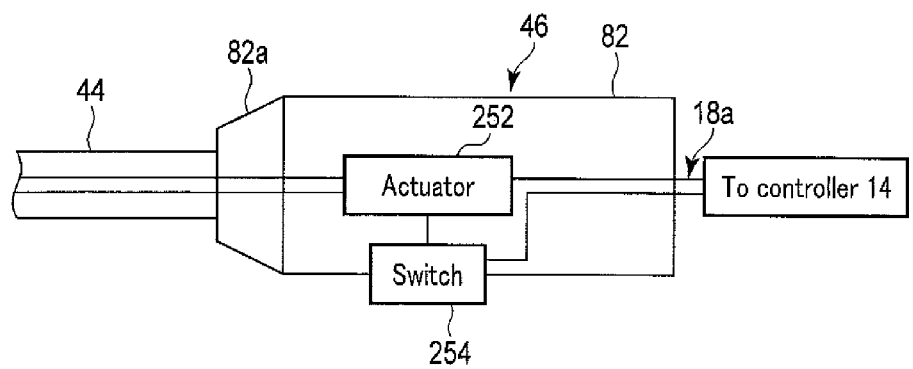
F I G. 13B

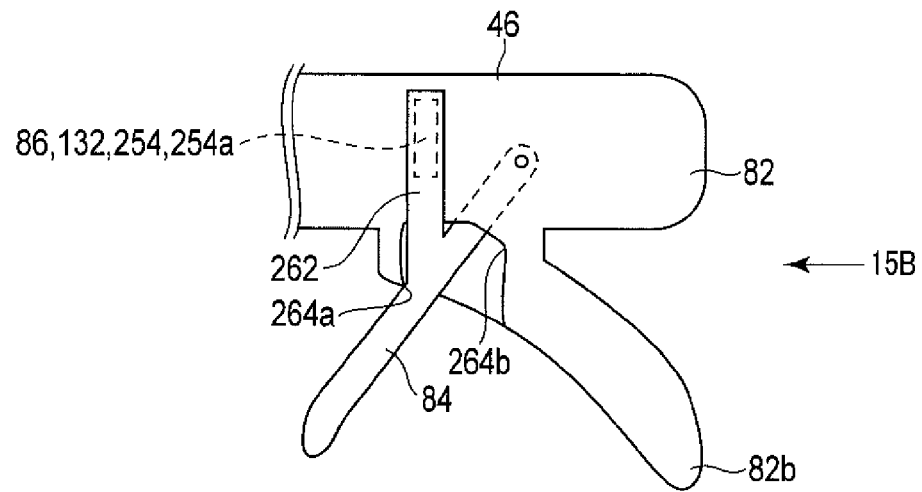
F I G. 15A
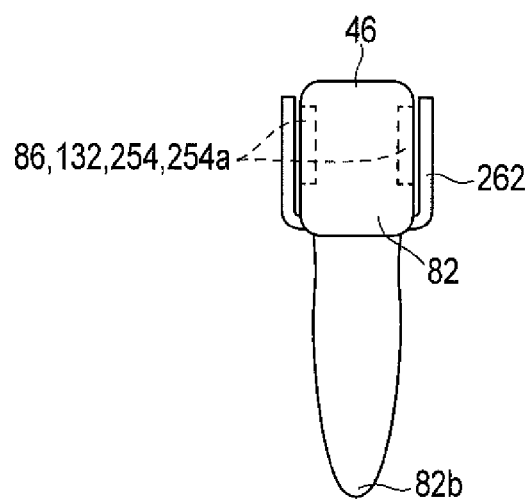
F I G. 15B

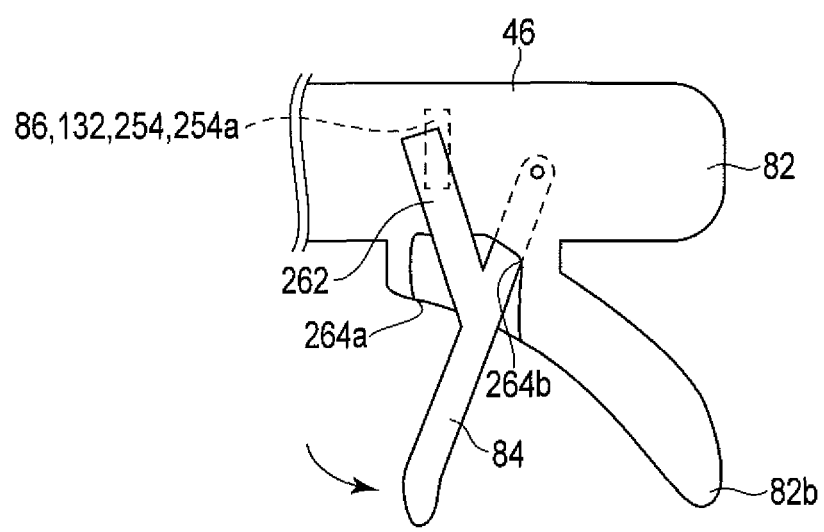
F I G. 15C

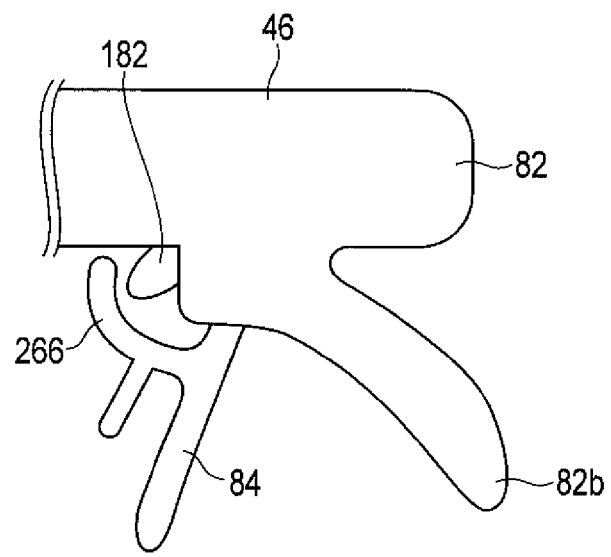
F I G. 16A
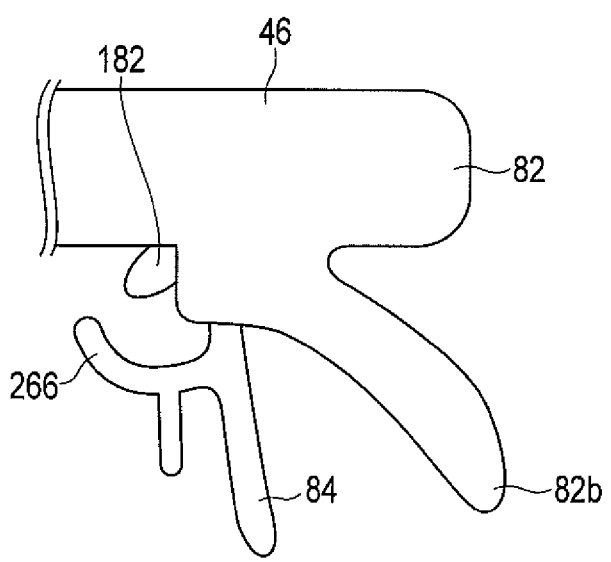
F I G. 16B

TREATMENT DEVICE

CROSS-REFERENCE TO RELATED APPLICATIONS

This is a Continuation application of PCT Application No. PCT/JP2014/084362, filed Dec. 25, 2014, and based upon and claiming the benefit of priority from prior U.S. Provisional Application No. 61/921,224, filed Dec. 27, 2013, the entire contents of which are incorporated herein by reference.

BACKGROUND OF THE INVENTION

1. Field of the Invention

The present invention relates to a treatment device used for performing a treatment, such as cutting, on a living tissue.

2. Description of the Related Art

For example, a treatment portion of a treatment device disclosed in Japanese Patent Application Publication No. 2001-170070 is capable of cutting a held living tissue by moving a cutter along an axial direction in a state where the living tissue is held.

BRIEF SUMMARY OF THE INVENTION

According to one aspect of the invention, a treatment device to treat a living tissue, includes: first and second holding portions including a longitudinal axis and including respective holding surfaces opening and closing in an opening/closing direction orthogonal to or substantially orthogonal to the longitudinal axis and capable of holding the living tissue therebetween; a rotary member including a working portion including an edge portion capable of cutting the living tissue by being rotated around a central axis equal to or substantially parallel with the longitudinal axis, the rotary member capable of moving the edge portion from the first holding portion to the second holding portion; a first guide portion provided in the first holding portion and capable of guiding the edge portion toward the second holding portion through the holding surface of the first holding portion; and a second guide portion provided in the second holding portion, and capable of guiding the edge portion to the second holding portion through the holding surface of the first holding portion, the second guide portion capable of cutting the living tissue in guiding the edge portion to the second holding portion through the holding surface of the first holding portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a schematic top view illustrating a first holding portion of the treatment device of the treatment system according to the first embodiment;

FIG. 4A is a schematic horizontal cross-sectional view illustrating a state where a working portion of a rotary member of the treatment device in the treatment system according to the first embodiment is disposed in a first guide portion of the first holding portion;

FIG. 4B is a schematic horizontal cross-sectional view illustrating a state where the working portion of the rotary member of the treatment device in the treatment system according to the first embodiment is moved from the state of being disposed in the first guide portion of the first holding portion illustrated in FIG. 4A toward a second guide portion of a second holding portion;

FIG. 4C is a schematic horizontal cross-sectional view illustrating a state where the working portion of the rotary member of the treatment device in the treatment system according to the first embodiment is disposed in the second guide portion, from the state of being disposed in the first guide portion of the first holding portion illustrated in FIG. 4A, via a state of being moved toward the second guide portion of the second holding portion illustrated in FIG. 4B;

FIG. 5A is a schematic perspective view illustrating a distal end portion of a driving portion and the working portion of the rotary member of the treatment device in the treatment system according to the first embodiment;

FIG. 5B is a schematic side view illustrating a state where a blade of the working portion of the rotary member of the treatment device in the treatment system according to the first embodiment illustrated in FIG. 5A is caused to project with respect to a holding surface of the first holding portion;

FIG. 8A is a schematic perspective view illustrating the distal end portion of the driving portion and the working portion of the rotary member of the treatment device in the treatment system according to a modification of the first embodiment;

FIG. 8B is a schematic side view illustrating a state where the blade of the working portion of the rotary member of the treatment device in the treatment system according to a modification of the first embodiment illustrated in FIG. 8A is caused to project with respect to the holding surface of the first holding portion;

FIG. 11A is a schematic side view of an operation portion of a treatment device in a treatment system according to a third embodiment;

FIG. 11B is a schematic top view of the operation portion of the treatment device in the treatment system according to the third embodiment;

FIG. 12C is a schematic side view illustrating an operating state of the opening/closing knob, the driving knob, and the interlocking member that are provided in the operation portion of the treatment device in the treatment system according to the third embodiment with respect to the operation portion main body, and a state where the driving knob is brought close to and closed with respect to the other end of the operation portion main body while the opening/closing knob is kept closed with respect to the other end of the operation portion main body, and abutment surfaces of the driving knob are caused to abut against the opening/closing knob directly after the fitting portion of the interlocking member is disengaged from the fitting receiving portion of the operation portion main body;

FIG. 12D is a schematic horizontal cross-sectional view of an opening/closing lever and a driving lever, taken along line 12D-12D in FIG. 12C of the treatment device in the treatment system according to the third embodiment;

FIG. 13A is a schematic side view of an operation portion of a treatment device in a treatment system according to a fourth embodiment;

FIG. 13B is a schematic block diagram of the operation portion of the treatment device in the treatment system according to the fourth embodiment as viewed from the top;

FIG. 15A is a schematic diagram illustrating an operation portion of a treatment device in a treatment system according to a sixth embodiment, and illustrating a state where an opening/closing knob is brought apart from the other end of the operation portion main body to open a first and second holding portions;

FIG. 15B is a schematic diagram illustrating the operation portion as viewed in a direction of an arrow 15B in FIG. 15A;

FIG. 15C is a schematic diagram illustrating the operation portion of the treatment device in the treatment system according to the sixth embodiment, and illustrating a state where the opening/closing knob is brought close to the other end of the operation portion main body to close the first and second holding portions;

FIG. 16A is a schematic diagram illustrating an operation portion of a treatment device in a treatment system according to a seventh embodiment, and illustrating a state where an opening/closing knob is brought apart from the other end of the operation portion main body to open a first and second holding portions; and FIG. 16B is a schematic diagram illustrating the operation portion of the treatment device in the treatment system according to the seventh embodiment, and illustrating a state where the opening/closing knob is brought close to the other end of the operation portion main body to close the first and second holding portions.

DETAILED DESCRIPTION OF THE INVENTION

Embodiments of the present invention will be explained hereinafter with reference to the drawings.

A first embodiment will be explained hereinafter with reference to FIG. 1A to FIG. 9B.

Figure 1A:
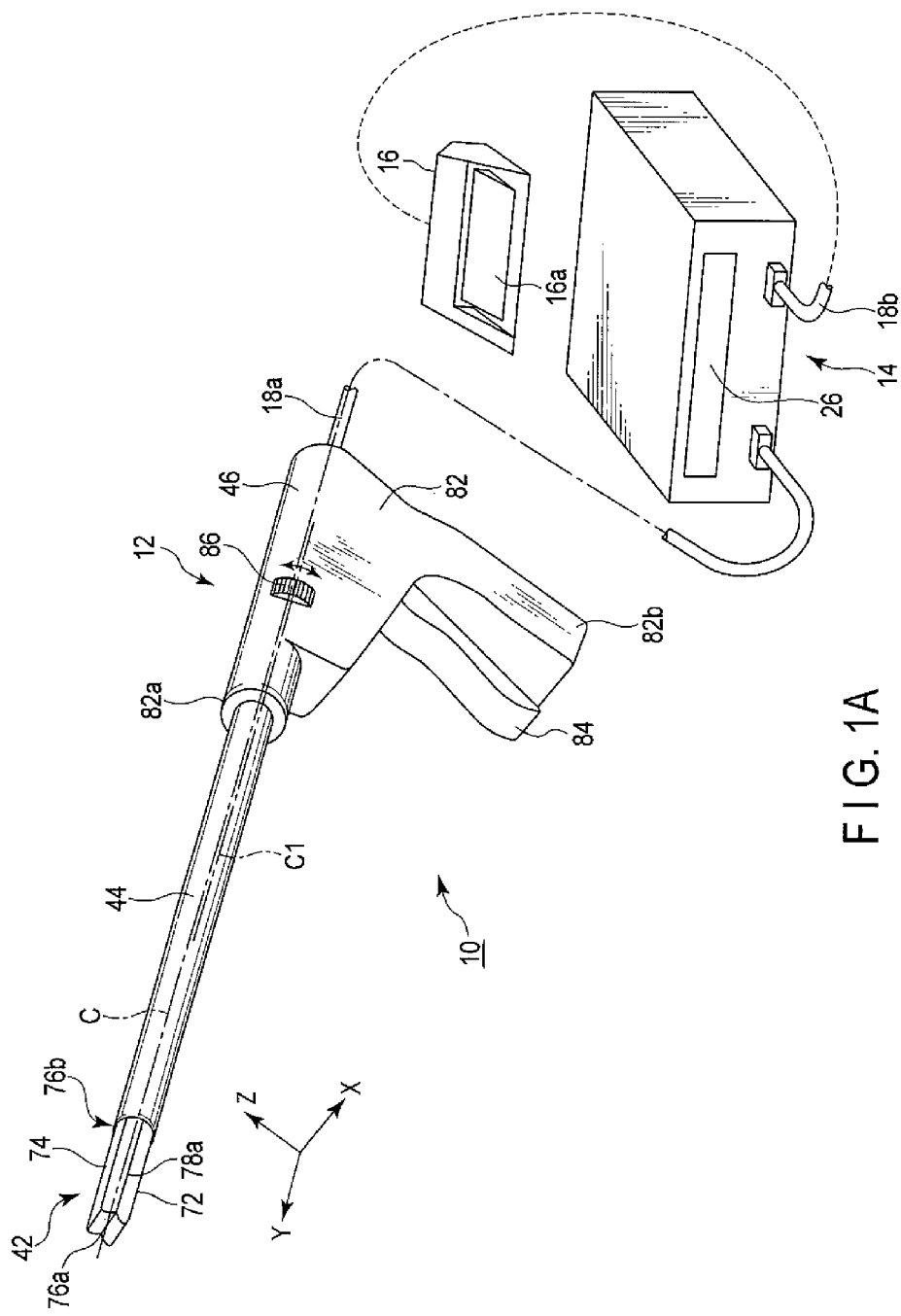
FIG. 1A is a schematic perspective view illustrating a treatment system according to a first embodiment.

As illustrated in FIG. 1A, a treatment system 10 according to the present embodiment includes a treatment device 12, and a controller 14 that applies energy to the treatment device 12. The controller 14 controls temperatures of first and second energy output portions 62 and 64 (described later) of the treatment device 12 to proper temperatures. The present embodiment illustrates an example of including the controller 14, but the controller 14 is not indispensable. Specifically, the first and second energy output portions 62 and 64 described later are not indispensable.

The controller 14 is connected with a foot switch 16 that includes a pedal 16a to turn on and off thermal energy to be applied to the treatment device 12. The treatment device 12 is electrically connected to the controller 14 with a first cable 18a formed of a bundle of a plurality of lead wires and/or signal wires, and the controller 14 is electrically connected to the foot switch 16 with a second cable 18b formed of a bundle of a plurality of lead wires and/or signal wires. The foot switch 16 is capable of inputting a signal to the controller 14 in response to an operation of the pedal 16a or the like. The controller 14 is capable of controlling the energy to be applied to the treatment device 12, based on the operation of the pedal 16a of the foot switch 16.

Figure 2:
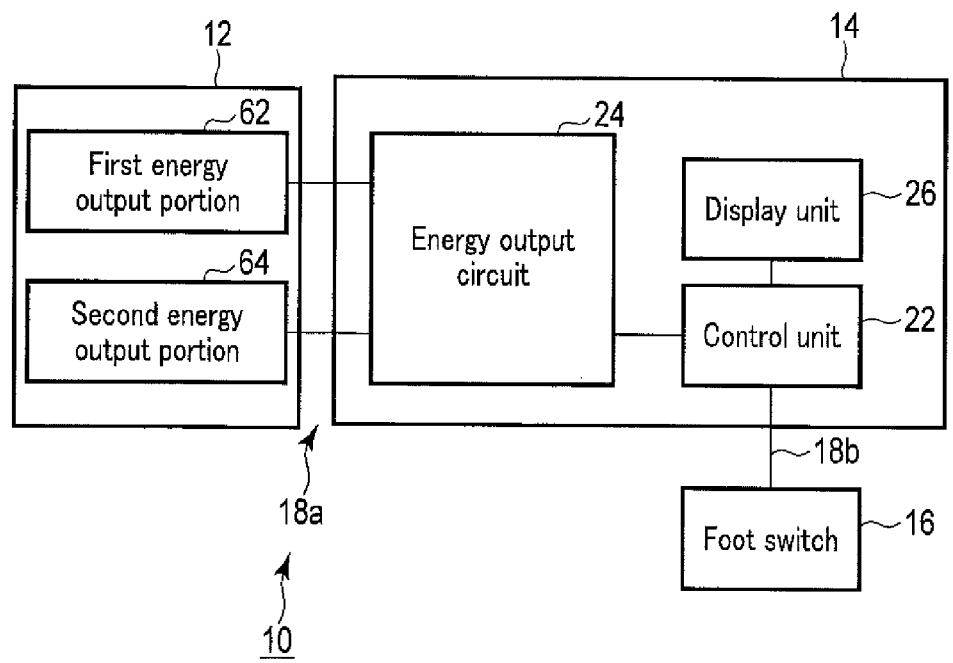
FIG. 2 is a schematic block diagram illustrating the treatment system according to the first embodiment.

As illustrated in FIG. 2, the controller 14 includes a control unit (CPU) 22, an energy output circuit (heat-generator driving circuit) 24, and a display unit 26. The control unit 22 controls the energy output circuit 24 and the display unit 26. The display unit 26 is used for displaying a state of the controller 14, and performing various settings. For example, a touch panel is preferably used as the display unit 26.

The foot switch 16 is connected with the control unit 22. When the pedal 16a of the foot switch 16 is pressed, respective energies are simultaneously output to the first and second energy output portions 62 and 64 described later from the energy output circuit 24.

As illustrated in FIG. 1A, the treatment device 12 includes a treatment portion 42 to treat a living tissue L, an insertion portion 44, and an operation portion 46. The operation portion 46 may be disposed directly on the proximal end of the treatment portion 42.

As illustrated in FIG. 1A, and FIG. 3 to FIG. 4C, the treatment portion 42 includes a pair of jaws (first and second jaws) 52 and 54 that are openable and closable and serve as holding portions for the living tissue, and the energy output portions (first and second energy output portions) 62 and 64 that are disposed on the jaws 52 and 54, respectively. The first jaw 52 and the first energy output portion 62 form a first holding portion 72 (see FIG. 1A) illustrated in FIG. 3, and the second jaw 54 and the second energy output portion 64 form a second holding portion 74 (see FIG. 1A).

The jaws 52 and 54 of the first and second holding portions 72 and 74 may be, for example, ceramics, resin having heat resistance and electric non-conductance, or an insulated metal material. A material having a heat insulating property is preferably used for the jaws 52 and 54 of the first and second holding portions 72 and 74.

As illustrated in FIG. 3, the first holding portion 72 has a longitudinal axis (longitudinal direction) Y defined by a distal end portion 76a and a proximal end portion 76b, and a width direction X defined in a direction orthogonal to the longitudinal axis Y. As illustrated in FIG. 3 to FIG. 4C, the width direction X includes a left end portion (one end) 78a disposed on the left side when the treatment portion 42 is viewed from the operation portion 46, and a right end portion (the other end) 78b disposed on the right side. Specifically, the width direction is defined by the left end portion (one end) 78a and the right end portion (the other end) 78b. In the first holding portion 72, a first holding surface 72a is defined by the distal end portion 76a, the proximal end portion 76b, one end 78a, and the other end 78b. In the same manner, the second holding portion 74 defines a second holding surface 74a that is opposed to the first holding surface 72a in parallel or substantially in parallel.

The energy output portions 62 and 64 of the first and second holding portions 72 and 74 are opposed to each other, and used as the holding surfaces 72a and 72b, respectively, that hold the living tissue L to be treated therebetween. The temperatures of the first and second energy output portions 62 and 64 preferably start to rise simultaneously, and rise to substantially the same temperature in substantially the same time.

The holding surface 72a of the first holding portion 72 is formed in a substantially flat shape that is long, for example, in a direction running along a central axis C of the insertion portion 44, and has the width direction X that is orthogonal to the longitudinal direction Y and smaller than the longitudinal direction Y. The second holding portion 74 is formed symmetrically or substantially symmetrically with the first holding portion 72. Specifically, the second holding surface 74a of the second holding portion 74 is formed in a substantially flat shape substantially symmetrically with the first holding surface 72a.

As illustrated in FIG. 1A, the holding surfaces 72a and 74a of the first and second holding portions 72 and 74 have an opening/closing direction (Z direction) in a direction orthogonal to or substantially orthogonal to the width direction X. Specifically, the opening/closing direction in which the first and second holding portions 72 and 74 are opened is orthogonal to or substantially orthogonal to the width direction X.

The operation portion 46 includes an operation portion main body 82 formed in a substantially L shape. The insertion portion 44 is disposed at one end (distal end) 82a of the operation portion main body 82. The cable 18a described above extends from the proximal end of the operation portion main body 82 located on substantially the same axis as that of the insertion portion 44.

The other end 82b of the operation portion main body 82 is a held portion that is held by the operator (user). The operation portion main body 82 includes a treatment portion opening/closing knob (opening/closing operation portion) 84 that is disposed side by side with the other end 82b. In the present embodiment, the knob 84 is disposed in front of the other end 82b of the operation portion main body 82. The knob 84 is rotatable with a pivotally supporting shaft (not illustrated) inside the operation portion main body 82, that is, the knob 84 can be brought close to and apart from the other end of the operation portion main body 82. By operating the knob 84, the first and second holding portions 72 and 74 of the treatment portion 42 are brought apart from each other to be opened, and close to each other to be closed, using a publicly-known mechanism. When the knob 84 is operated, the first and second holding portions 72 and 74 are opened and closed in the Z direction illustrated in FIG. 1A, with publicly-known means such as a wire and a rod disposed inside the insertion portion 44. One or both of the first and second holding portions 72 and 74 may be moved by an operation of the knob 84 of the operation portion 46. With this structure, the first and second holding portions 72 and 74 are relatively openable and closable.

The operation portion main body 82 also includes a driving dial (rotation operation portion) 86 to rotate a rotary member 92 described later around a central axis C1 thereof. The dial 86 is not limited to a disk shape, but may have a fan shape. The dial 86 is rotatable with a pivotally support shaft (not illustrated) inside the operation portion main body 82. The dial 86 is located inside the operation portion main body 82, and part of the dial 86 projects and is exposed to the outside of the operation portion main body 82. With this structure, by operating the dial 86 in a proper direction with the user's finger, the rotary member 92 is rotated around the central axis C. For example, when the dial 86 is rotated upward from the lower side in FIG. 1A, a blade 98 described later is moved from the first holding portion 72 to the second holding portion 74 to cut the living tissue. When the dial 86 is rotated downward from the upper side, the blade 98 is retracted from the second holding portion 74 into the first holding portion 72. The rotating amount of the dial 86 preferably corresponds to the rotation amount of the rotary member 92 in one-to-one correspondence. The dial 86 is prevented from rotating due to friction or the like in a natural state, and adjusted to be rotated by a user's operation.

As illustrated in FIG. 1A, the rotary member 92 is disposed inside the treatment portion 42 and the insertion portion 44. The rotary member 92 has the central axis C1 that is suitably parallel with the longitudinal axis Y. The proximal end of the rotary member 92 is coupled with the dial (rotation operation portion) 86 of the operation portion 46. With this structure, when the dial 86 is rotated, the rotary member 92 is rotated. The central axis C1 of the rotary member 92 may be shifted from the central axis C of the insertion portion 44, although they may agree according to the position of the blade 98 described later. The present embodiment illustrates an example where the central axis C1 of the rotary member 92 is shifted from the central axis C of the insertion portion 44.

As illustrated in FIG. 5A, the rotary member 92 includes a driving portion 94 that is rotated by the dial 86, and a blade-shaped working portion 96 that is disposed at a distal end of the driving portion 94 and formed of a curved surface or the like that is operated to follow the operation of the driving portion 94. The driving portion 94 has a suitable tube shape such as a cylindrical shape as illustrated in FIG. 5A, but the shape is not limited to a tube shape. The driving portion 94 may suitably be, for example, a ½ pipe, as long as it can transmit the operation of the dial 86 to the working portion 96. The rotary member 92 is formed of a hard material. For example, a stainless steel is preferably used as the material.

The working portion 96 includes a pair of edge portions 96a and 96b with an angle of a range from substantially a ½ pipe to 1/12 pipe, for example. A distal end edge portion 96c of the working portion 96 is suitably formed in an arc shape.

In the present embodiment, one edge portion 96a in the edge portions 96a and 96b includes the blade (cutting portion) 98. The blade 98 is preferably continuously formed from a distal end portion 98a to a proximal end portion 98b of the edge portion 96a. In the present embodiment, the blade 98 is parallel with the central axis C1 of the rotary member 92, and parallel with the holding surface 72a of the first holding portion 72, as illustrated in FIG. 5B. The central axis C1 of the rotary member 92 preferably agrees with the pivotally supporting shaft of the dial 86. The blade 98 can be formed with a desired length. The length of the blade 98 is suitably longer than a length of the width direction X, that is, a length between the left end portion (one end) 78a and the right end portion (the other end) 78b described later. For this reason, the length of first and second openings 112 and 114, and the length of first and second recessed grooves 122 and 124 along the longitudinal axis Y are suitably longer than the length in the width direction X.

In the present embodiment, the blade 98 is not only formed on one edge portion 96a of the working portion 96, but may be formed on the other edge portion 96b.

As illustrated in FIG. 3 to FIG. 4C, first and second guide portions 102 and 104 that are capable of guiding the working portion 96 of the rotary member 92 are disposed in the treatment portion 42. The first guide portion 102 is provided in the first holding portion 72, and the second guide portion 104 is provided in the second holding portion 74. The first and second guide portions 102 and 104 are capable of guiding the working portion 96, that is, the blade 98, to the second holding portion 74 through the first holding surface 72a of the first holding portion 72. The living tissue can be cut when the blade 98 is guided to the second holding portion 74 through the holding surface 72a of the first holding portion 72.

The first guide portion 102 includes the first opening 112 provided in the holding surface 72a of the first holding portion 72 and provided between the left end portion (one end) 78a and the right end portion (the other end) 78b in the width direction X. The blade 98 is put into and out of the first opening 112. The second guide portion 104 includes the second opening 114 provided in the holding surface 74a of the second holding portion 74 and provided between the left end portion 78a and the right end portion 78b in the width direction X. The blade 98 is put into and out of the second opening 114, and the second opening 114 is opposed to the first opening 112.

As illustrated in FIG. 3, the first opening 112 is suitably formed in the substantial center between the left end portion 78a and the right end portion 78b in the width direction X. However, the first opening 112 may be disposed close to the left end portion 78a or the right end portion 78b in the width direction X. The second opening 114 is suitably formed in the substantial center between the left end portion 78a and the right end portion 78b in the width direction X. However, the second opening 114 may be disposed close to the left end portion 78a or the right end portion 78b in the width direction X. In any case, the first and second openings 112 and 114 are opposed to each other.

The first guide portion 102 includes a curved or inclined first recessed groove 122 that is continuous with the first opening 112 from the holding surface 72a of the first holding portion 72 toward the back surface 72b of the first holding portion 72. The second guide portion 104 includes a curved or inclined second recessed groove 124 that is continuous with the second opening 114 from the holding surface 74a of the second holding portion 74 toward a back surface 74b of the second holding portion 74.

The first recessed groove 122 extends toward the left end portion (one end) 78a in the width direction X as the first recessed groove 122 comes close to the back surface 72b from the holding surface 72a of the first holding portion 72. The second recessed groove 124 extends in the same direction as the direction in which the first recessed groove 122 extends, as the second recessed groove 124 comes close to the back surface 74b from the holding surface 74a of the second holding portion 74.

The length of the working portion 96 and the length of the blade 98 illustrated in FIG. 5A and FIG. 5B may be properly set. Specifically, the length of the first opening 112 and the second opening 114 along the longitudinal axis Y may be properly set.

The following is an explanation of the function of the treatment system 10 according to the present embodiment.

As illustrated in FIG. 4A, the edge portion 96a of the working portion 96 of the rotary member 92, that is, the blade 98 is retracted in the first guide portion 102, to prevent the edge portion 96a, that is, the blade 98 from projecting from the first holding surface 72a through the first opening 112.

The treatment portion 42 is caused to face the living tissue to be treated. In this state, the first and second holding portion 72 and 74 are opened in the opening/closing direction Z, to hold the living tissue between the first and second holding surfaces 72a and 74a.

Energy is output from the controller 14 to the first and second holding surfaces 72a and 74a, that is, the first and second energy output portions 62 and 64, to properly heat, dehydrate, and degenerate the living tissue abutting against the holding surfaces 72a and 74a. For this reason, the living tissue held between the first and second holding portions 72 and 74 and abutting against the holding surfaces 72a and 74a is, for example, coagulated.

For example, when the coagulated living tissue is cut, the dial 86 of the operation portion main body 82 is rotated upward from the lower side in FIG. 1A with a user's finger or the like. The rotary member 92 is rotated by rotation of the dial 86. In the rotary member 92, the driving portion 94 is rotated around the central axis C. For this reason, the working portion 96 is also rotated to follow the rotation of the driving portion 94.

Accordingly, as illustrated in FIG. 4A to FIG. 4C, the edge portion 96a, that is, the blade 98 of the working portion 96 is guided to the second recessed groove 124 of the second guide portion 104 through the first groove 122 of the first guide portion 102, the first opening 112 of the first guide portion 102, and the second opening 114 of the second guide portion 104. Specifically, the rotary member 92 is capable of moving the edge portion 96a of the working portion 96 from the first holding portion 72 toward the second holding portion 74. In the operation, the edge portion 96a, that is, the blade 98 moves between the first opening 112 of the first holding portion 72 and the second opening 114 of the second holding portion 74, and thereby the living tissue held between the holding surfaces 72a and 74a is cut.

As described above, by rotating the dial 86 around the rotation axis C1, the contacting living tissue can be cut by merely bringing the blade 98 into contact with the living tissue substantially simultaneously by the length of the blade 98 extending in the longitudinal direction Y and moving the blade 98 to the second guide portion 104. Accordingly, the living tissue can be cut by merely moving the edge portion 96a, that is, the blade 98 by a distance substantially from the first opening 112 to the second opening 114.

When the treatment device is formed with a structure of moving the blade from the proximal ends to the distal ends of the first and second openings 112 to 114 (the structure of moving the blade along the longitudinal axis Y), the distance to move the blade to cut the living tissue with the blade is clearly longer than the distance between the first and second openings 112 and 114. By contrast, the edge portion 96a, that is, the blade 98 according to the present embodiment is capable of cutting the living tissue by moving the blade 98 by a distance between the first and second openings 112 and 114, or a distance slightly longer than the distance. Accordingly, the treatment device 12 according to the present embodiment markedly reduces the moving distance of the edge portion 96a, that is, the blade 98, to cut the living tissue. This structure also reduces the moving distance of the dial 86 of the operation portion 46, and enables easy performance of an operation of cutting the living tissue.

Figure 1B:
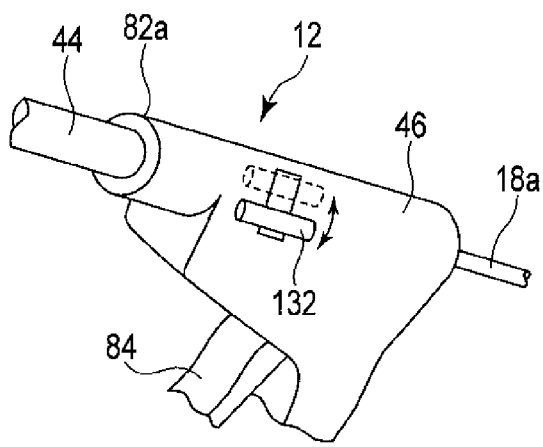
FIG. 1B is a schematic perspective view illustrating a modification of a rotation operation portion disposed in an operation portion of a treatment device of the treatment system according to the first embodiment.

Although the present embodiment illustrates the example of disposing the dial 86 illustrated in FIG. 1A in the operation portion main body 82 of the operation portion 46, the treatment device can also be used in the same manner, using a lever 132 illustrated in FIG. 1B. The rotation distance of the lever 132 may be any distance that enables the blade 98 to securely cut the living tissue.

The present embodiment illustrates the example where the holding surface 72a of the first holding portion 72 is parallel with the edge portion 96a, that is, the blade 98, as illustrated in FIG. 5B.

Figure 6A:
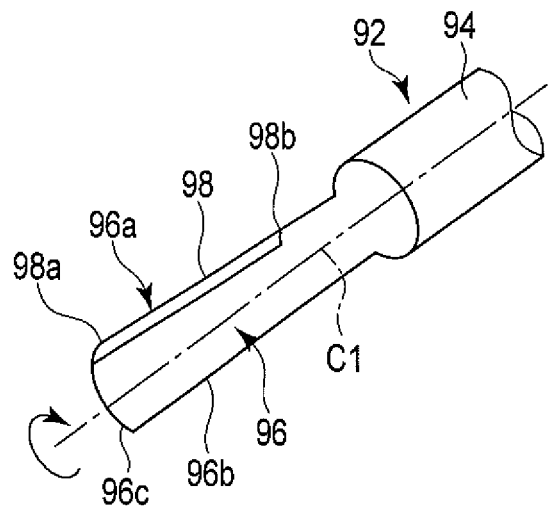
FIG. 6A is a schematic perspective view illustrating the distal end portion of the driving portion and the working portion of the rotary member of the treatment device in the treatment system according to a modification of the first embodiment.
Figure 6B:
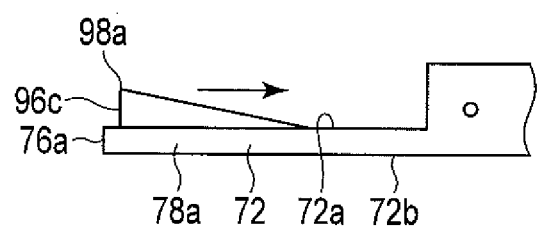
FIG. 6B is a schematic side view illustrating a state where the blade of the working portion of the rotary member of the treatment device in the treatment system according to a modification of the first embodiment illustrated in FIG. 6A is caused to project with respect to the holding surface of the first holding portion.

As illustrated in FIG. 6A, the blade 98 includes the distal end portion 98a and the proximal end portion 98b along the longitudinal axis Y. As illustrated in FIG. 6B, the blade 98 may suitably be formed to be not parallel with the holding surface 72a of the first holding portion 72, but to project in the order of the distal end portion 98a and proximal end portion 98b when the blade 98 in the first guide portion 102 is caused to project from the holding surface 72a of the first holding portion 72. In the operation, the force of holding the living tissue with the treatment portion 42 is larger on the side close to the proximal end portion 76b of the treatment portion 42 than that on the side close to the distal end portion 76a of the treatment portion 42. This structure prevents the living tissue from moving between the first and second holding surfaces 72a and 74a in cutting, and prevents cutting failure.

Figure 7A:
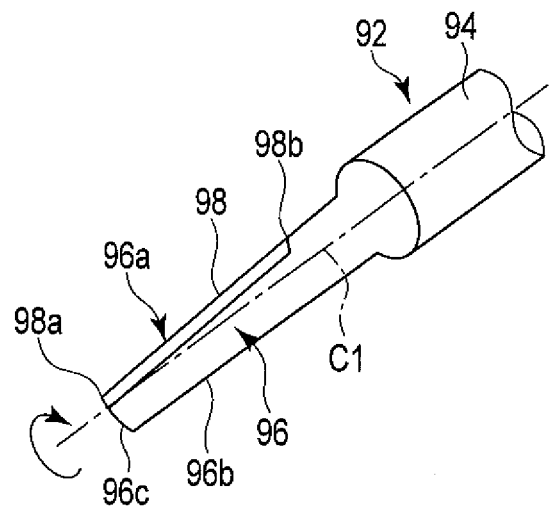
FIG. 7A is a schematic perspective view illustrating the distal end portion of the driving portion and the working portion of the rotary member of the treatment device in the treatment system according to a modification of the first embodiment.
Figure 7B:
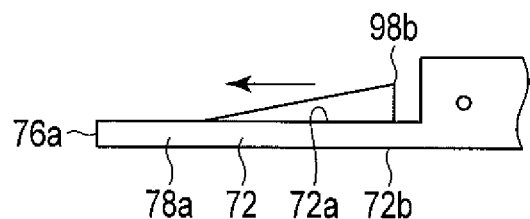
FIG. 7B is a schematic side view illustrating a state where the blade of the working portion of the rotary member of the treatment device in the treatment system according to a modification of the first embodiment illustrated in FIG. 7A is caused to project with respect to the holding surface of the first holding portion.

As illustrated in FIG. 7A, the blade 98 includes the distal end portion 98a and the proximal end portion 98b along the longitudinal axis Y. As illustrated in FIG. 7B, the blade 98 may suitably be formed to be not parallel with the holding surface 72a of the first holding portion 72, but to project in the order of the proximal end portion 98b and distal end portion 98a when the blade 98 in the first guide portion 102 is caused to project from the holding surface 72a of the first holding portion 72. In the operation, because the blade 98 cuts the living tissue to push out the living tissue toward the distal end portion 76a of the treatment portion 42, the living tissue is prevented from being stuffed into the proximal end portion 76b of the treatment portion 42 after the living tissue is cut.

As illustrated in FIG. 8A, the blade 98 includes the distal end portion 98a and the proximal end portion 98b along the longitudinal axis Y. The blade 98 also includes a central portion 98C between the distal end portion 98a and the proximal end portion 98b. As illustrated in FIG. 8B, the blade 98 may suitably be formed to be not parallel with the holding surface 72a of the first holding portion 72, but to project in the order of the distal end portion 98a and/or the proximal end portion 98b, and the central portion 98c between the distal end portion 98a and the proximal end portion 98b, when the blade 98 in the first guide portion 102 is caused to project from the holding surface 72a of the first holding portion 72. In the operation, the force of holding the living tissue with the treatment portion 42 is larger on the side close to the proximal end portion 76b of the treatment portion 42 than that on the side close to the distal end portion 76a of the treatment portion 42. This structure prevents the living tissue from moving between the first and second holding surfaces 72a and 74a in cutting the living tissue with the blade 98, in particular, with the distal end portion 98a, and prevents cutting failure. In addition, because the blade 98, in particular, the proximal end portion 98b cuts the living tissue to push out the living tissue toward the distal end portion 76a of the treatment portion 42, the living tissue is prevented from being stuffed into the proximal end portion 76b of the treatment portion 42 when or after the living tissue is cut.

Figure 9A:
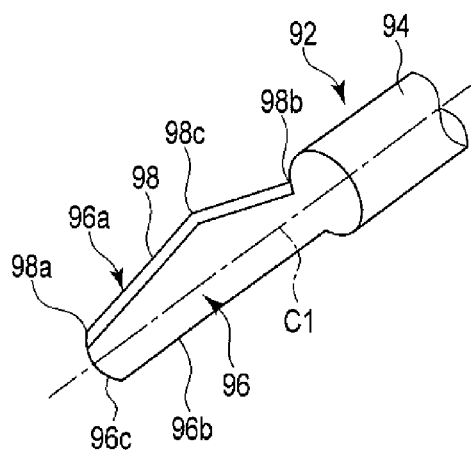
FIG. 9A is a schematic perspective view illustrating the distal end portion of the driving portion and the working portion of the rotary member of the treatment device in the treatment system according to a modification of the first embodiment.
Figure 9B:
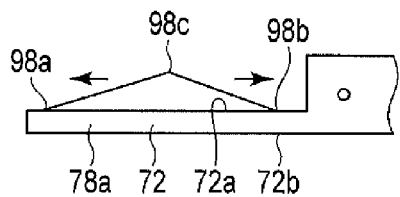
FIG. 9B is a schematic side view illustrating a state where the blade of the working portion of the rotary member of the treatment device in the treatment system according to a modification of the first embodiment illustrated in FIG. 9A is caused to project with respect to the holding surface of the first holding portion.

As illustrated in FIG. 9A and FIG. 9B, the blade 98 includes the distal end portion 98a and the proximal end portion 98b along the longitudinal axis Y. The blade 98 also includes a central portion 98C between the distal end portion 98a and the proximal end portion 98b. As illustrated in FIG. 9B, the blade 98 may suitably be formed to be not parallel with the holding surface 72a of the first holding portion 72, but to project in the order of the central portion 98c between the distal end portion 98a and the proximal end portion 98b, and the distal end portion 98a and/or the proximal end portion 98b, when the blade 98 in the first guide portion 102 is caused to project from the holding surface 72a of the first holding portion 72.

The present embodiment illustrates the example where the energy output portions 62 and 64 are heaters, but various elements may be used as the energy output portions 62 and 64, as long as they can apply energy to the living tissue to treat the living tissue, such as high-frequency electrodes.

As illustrated in FIG. 4A to FIG. 4C, the first recessed groove 122 of the first guide portion 102 and the second recessed groove 124 of the second guide portion 104 are substantially symmetrical. However, it is preferable that the first recessed groove 122 of the first guide portion 102 is larger than the second recessed groove 124 of the second guide portion 104.

The present embodiment illustrates the example where the working portion 96 of the rotary member 92 is rotated as illustrated in FIG. 4A to FIG. 4C, but similar functions and effects can be obtained by rotating the working unit 96 in an opposite direction. In this case, the dial 86 is preferably disposed on the right side surface of the operation portion main body 82, not the left side surface illustrated in FIG. 1A.

Figure 10:
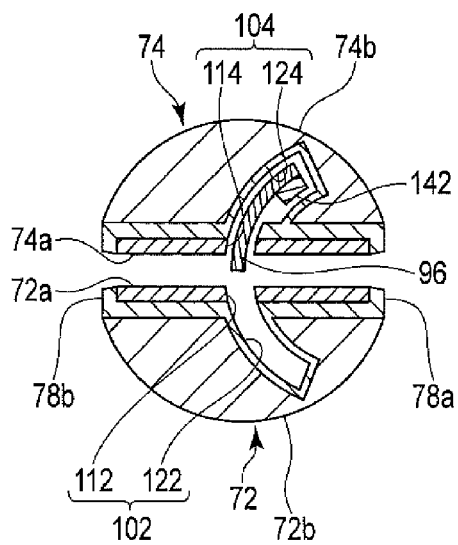
FIG. 10 is a schematic horizontal cross-sectional view illustrating a state where a working portion of a rotary member of a treatment device in a treatment system according to a second embodiment is disposed in a second guide portion, from a state of being disposed in a first guide portion of a first holding portion.

The following is an explanation of a second embodiment with reference to FIG. 10. The present embodiment is a modification of the first embodiment. The same members or members having the same function as the members explained in the first embodiment are denoted by the same respective reference numerals, and detailed explanation thereof is omitted.

In the present embodiment, the edge portion 96a of the working unit 96 of the rotary member 92 includes an energy output portion 142 together with the blade 98, or instead of the blade 98. Specifically, the edge portion 96a of the working portion 96 may suitably include the energy output portion 142 such as a heater. The structure enables the treatment device to perform a hot cut, in which heat from the energy output portion 142 is conducted to the edge portion 96a, and thereby the living tissue is provided with heat and cut. For this reason, the working portion 96 of the rotary member 92 of the treatment device 12 according to the present embodiment preferably is formed of a material having moderate thermal conductivity.

The energy output portion 142 according to the present embodiment is, for example, connected to the controller 14. For this reason, the working portion 96 can be heated with the energy output portion 142 by heat transfer action from the energy output portion 142. When the living tissue is cut in a state of heating the working portion 96, the edge portion 96a of the working portion 96 is caused to abut against the living tissue, to dehydrate the living tissue with the heat and cauterize and incise the living tissue. The living tissue can be cut in the same manner as explained in the first embodiment, also with the structure of heating the working portion 96 or the like.

When the edge portion 96a includes the blade 98, the treatment device is enabled to cut the living tissue more easily, together with the heating function by the energy output portion 142.

When the energy output portion 142 explained in the present embodiment is present, there are cases where the first energy output portion 62 is disposed in the first holding portion 72 and the second energy output portion 64 is not disposed in the second holding portion 74, or where the second energy output portion 64 is disposed in the second jaw 54 and the first energy output portion 62 is not disposed in the first jaw 52. In addition, there are cases where the first energy output portion 62 is not disposed in the first holding portion 72, and the second energy output portion 64 is not disposed in the second holding portion 74.

Specifically, although the first embodiment illustrates the structure in which at least one of the first and second holding portions 72 and 74 includes the energy output portions 62 and 64, respectively, that are capable of treating the living tissue by applying energy to the living tissue, the energy output portions 62 and 64 may not be disposed in the treatment portion 42. Instead, the energy output portion 142 heats the working portion 96, to easily cut the living tissue.

The following is an explanation of a third embodiment, with reference to FIG. 11A to FIG. 12D. The embodiment is a modification of the first embodiment. The same members or members having the same function as the members explained in the first embodiment are denoted by the same respective reference numerals, and detailed explanation thereof is omitted.

The present embodiment illustrates a modification of a mechanism to operate the rotary member 92, instead of the dial 86 explained in the first embodiment.

As illustrated in FIG. 11A, a bevel gear 170 is disposed inside the operation portion main body 82, as part of a rotation operating portion to rotate the rotary member 92. When the bevel gear 170 is driven, the bevel gear 170 transmits its motive power to the rotary member 92, to rotate the rotary member 92 around the central axis C1. The operation portion main body 82 includes a driving knob (rotation operating portion) 182 to drive the bevel gear 170 that transmits the motive power to rotate the rotary member 92, that is, to rotate the rotary member 92 around the central axis C1, as part of the rotation operating portion to rotate the rotary member 92.

When the driving knob 182 is moved from a state distant from the other end 82b of the operation portion main body 82 to a state close to the other end 82b, the bevel gear 170 is driven, and the rotary member 92 is rotated around the central axis C1. In the operation, the blade 98 of the working portion 96 of the rotary member 92 is moved from the first guide portion 102 of the first holding portion 72 to the second guide portion 104 of the second holding portion 74.

When the driving knob 182 is moved from the state close to the other end 82b of the operation portion main body 82 to the state distant from the other end 82b, the bevel gear 170 is driven, and the rotary member 92 is rotated around the central axis C1. In the operation, the working portion 96 of the rotary member 92 is moved from the second guide portion 104 of the second holding portion 74 to the first guide portion 102 of the first holding portion 72.

The treatment device 12 can also cut the living tissue in the same manner as the treatment devices 12 explained in the first and second embodiments, with the structure of providing the operation portion 46 with the driving knob 182 that causes the rotary member 92 to cooperate via the bevel gear 170.

Figure 12A:
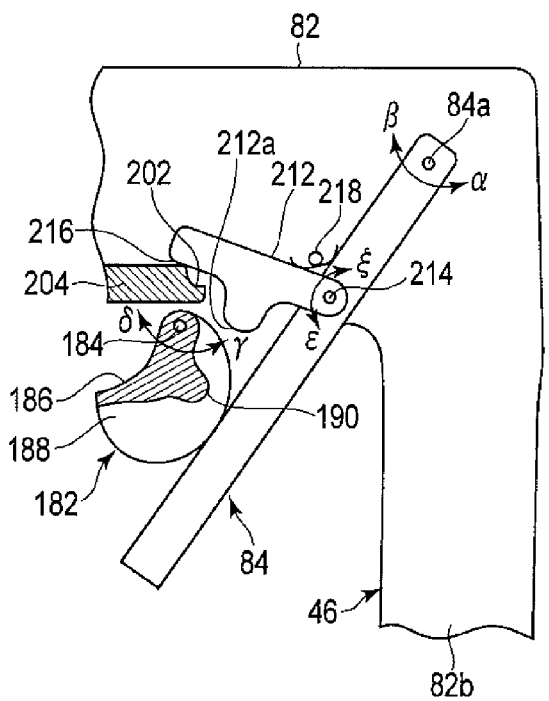
FIG. 12A is a schematic side view illustrating an operating state of an opening/closing knob, a driving knob, and an interlocking member that are provided in the operation portion of the treatment device in the treatment system according to the third embodiment with respect to an operation portion main body, and a state where the opening/closing knob and the driving knob are opened apart from the other end of the operation portion main body and a fitting portion of the interlocking member is disengaged from a fitting receiving portion of the operation portion main body.
Figure 12B:
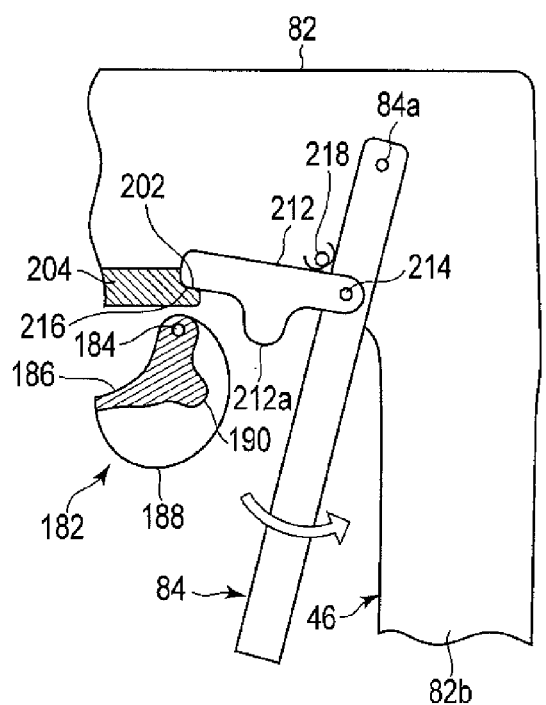
FIG. 12B is a schematic side view illustrating an operating state of the opening/closing knob, the driving knob, and the interlocking member that are provided in the operation portion of the treatment device in the treatment system according to the third embodiment with respect to the operation portion main body, and a state where the opening/closing knob is brought close to and closed with respect to the other end of the operation portion main body while the driving knob is kept opened and apart from the other end of the operation portion main body, and the fitting portion of the interlocking member is fitted into the fitting receiving portion of the operation portion main body.

As illustrated in FIG. 12A to FIG. 12C, the driving knob 182 includes a pivotally supporting shaft 184 coupled with the bevel gear 170, a finger placing portion 186 on which the forefinger or the middle finger is placed, a pair of abutting surfaces (first abutment portion) 188 caused to abut against the opening/closing knob 84, and a projection (second abutment portion) 190 to abut against a projection 212a of an interlocking member 212 described later. The driving knob 182 is rotatable in a first direction γ and a second direction δ with the pivotally supporting shaft 184 disposed inside the operation portion main body 82. The finger placing portion 186 of the driving knob 182 projects outward from a lower end of the operation portion main body 82, and is disposed on the front side of the other end 82b of the operation portion main body 82. With this structure, the finger placing portion 186 of the driving knob 182 can be brought close to and apart from the other end 82b of the operation portion main body 82.

When the finger placing portion 186 of the driving knob 182 is operated to be brought close to the other end 82b of the operation portion main body 82, the bevel gear 170 is driven to rotate the rotary member 92, and the edge portion 96a of the working portion 96 of the rotary member 92 is moved from the first guide portion 102 to the second guide portion 104. When the finger placing portion 186 of the driving knob 182 is operated to be brought apart from the other end 82b of the operation portion main body 82, the bevel gear 170 is driven to rotate the rotary member 92, and the edge portion 96a of the working portion 96 of the rotary member 92 is moved from the second guide portion 104 to the first guide portion 102.

As illustrated in FIG. 12A to FIG. 12D, the operation portion main body 82 includes a support portion 204 that includes a fitting receiving portion (engagement receiving portion) 202 on which a fitting portion (engagement portion) 216 of an interlocking member 212 described later is placed, and with which the fitting portion 216 is fitted or engaged. The fitting receiving portion 202 has a vertical cross section having substantially an L shape. The fitting receiving portion 202 has a recessed shape on the internal side of the operation portion main body 82, and has a projecting shape on the lower end side (external side).

The treatment portion opening/closing knob (opening/closing operation portion) 84 supports the interlocking member 212 that interlocks and moves together, with a rotating shaft 214. The rotating shaft 214 is supported on the proximal end of the interlocking member 212. The interlocking member 212 is rotatable in a first direction ε and a second direction ζ with the rotating shaft 214. The interlocking member 212 moves together with an input of an operation to the opening/closing knob 84. When the opening/closing knob 84 is rotated in the first direction α around the pivotally supporting shaft 84a, the interlocking member 212 is rotated in the first direction ε or the second direction ζ, and prevents the opening/closing knob 84 from rotating in the second direction β when the interlocking member 212 is engaged with the operation portion main body 82.

The interlocking member 212 includes, at its distal end, a fitting portion 216 that can be fitted into the fitting receiving portion 202 of the operation portion main body 82. An elastic member 218 is disposed between the opening/closing operating lever 84 and the interlocking member 212. The elastic member 218 urges the fitting portion 216 of the interlocking member 212 toward the fitting receiving portion 202 of the operation portion main body 82.

As illustrated in FIG. 12A to FIG. 12C, the interlocking member 212 includes a projection 212a that projects toward the lower end of the operation portion main body 82. In other words, the interlocking member 212 includes the projection 212a that projects toward the driving knob 182 to abut against the projection 190 of the driving knob (second operation input member) 182.

As illustrated in FIG. 12A to FIG. 12D, the projection 190 of the driving knob 182 is at a position closer to the finger placing portion 186 than the proximal end side edge portions of the abutting surfaces 188, and is formed between the abutting surfaces 188. For this reason, a space 188a is formed between the projection 190 and the abutting surfaces 188. As illustrated in FIG. 12C, the interlocking member 212 does not abut against the abutting surfaces 188 of the driving knob 182, but the projection 190 of the driving knob 182 abuts against the projection 212a of the interlocking member 212. Thereafter, when the driving knob 182 is rotated in the first direction γ in the state where the interlocking member 212 is fitted on the operation portion main body 212, the driving knob 182 is caused to abut against the interlocking member 212 earlier than the timing at which the driving knob 182 abuts against the opening/closing knob 84. The abutting surfaces 188 are formed as, for example, plane cams. When the contact position between the abutting surfaces 188 of the driving knob 182 and the opening/closing knob 84 illustrated in FIG. 12A is compared with the contact position between the abutting surfaces 188 of the driving knob 182 and the opening/closing knob 84 illustrated in FIG. 12C, the former has a smaller distance between the contact position and the pivotally supporting shaft 184 of the driving knob 182. When the opening/closing knob 84 in the position illustrated in FIG. 12C is returned to the position illustrated in FIG. 12A, the abutting surfaces 188 formed as plane cams are adjusted to move the blade 68 of the working portion 96 from the second guide portion 104 to the first guide portion 102, while maintaining the state where the first and second holding portions 72 and 74 are closed as much as possible. This structure prevents the working portion 96 from being guided from the first guide portion 102 to the second guide portion 104 in a state where no living tissue is held.

The following is a functional explanation of the treatment system 10 according to the present embodiment with reference to FIG. 12A to FIG. 12C.

The opening/closing knob 84 is operated to be rotated in the first direction α from a state where the opening/closing knob 84 and the driving knob 182 are in the positions illustrated in FIG. 12A, to bring the opening/closing knob 84 close to the other end 82b of the operation portion main body 82. In this state, the interlocking member 212 is urged toward the support portion 204 of the operation portion main body 82 with the elastic member 218. For this reason, the fitting portion 216 of the interlocking member 212 is moved closer to the fitting receiving portion 202 of the support portion 204 while abutting against the support portion 204 of the operation portion main body 82. Specifically, the fitting portion 216 of the interlocking member 212 supported by the rotating shaft 214 is moved closer to the fitting receiving portion 202 of the operation portion main body 82, together with movement of the opening/closing knob 84. In the movement, the interlocking member 212 may be relatively moved in the second direction ζ with respect to the opening/closing knob 84, with the rotating shaft 214. Thereafter, as illustrated in FIG. 12B, the fitting portion 216 of the interlocking member 212 is fitted into or engaged with the fitting receiving portion 202 of the operation portion main body 82. In the operation, the interlocking member 212 is rotated in the first direction ε with respect to the opening/closing knob 84 with the rotating shaft 214.

In this state, the elastic member 218 applies an urging force to the interlocking member 212, to maintain the state where the fitting portion 216 of the interlocking member 212 is fitted into the fitting receiving portion 212. This structure prevents the opening/closing knob 84 from being rotated in the second direction β.

When the opening/closing knob 84 is rotated in the first direction α, the living tissue can be held between the holding surfaces 72a and 74a. In addition, the living tissue held between the holding surfaces 72a and 74a can be properly treated using energy.

After the living tissue is properly treated, the driving knob 182 is rotated in the first direction γ, to be brought close to the opening/closing knob 84. In this state, as illustrated in FIG. 12C, the driving knob 182 is caused to abut against the interlocking member 212 earlier than the timing at which the driving knob 182 abuts against the opening/closing knob 84. Specifically, the projection 190 of the driving knob 182 is caused to abut against the projection 212a of the interlocking member 212. Thereafter, the interlocking member 212 is pushed up in the second direction ζ around the rotating shaft 214 against the urging force of the elastic member 218, to release the state in which the fitting portion 216 is fitted into or engaged with the fitting receiving portion 202. Thereafter, the abutting portions 188 of the driving knob 182 are caused to abut against the opening/closing knob 84.

Specifically, when the abutting portions 188 of the driving knob 182 are caused to abut against the opening/closing knob 84, the interlocking member 212 has already been rotated in the second direction ζ around the rotating shaft 214, to avoid the state in which the fitting portion 216 is fitted into or engaged with the fitting receiving portion 202.

When the driving knob 182 is rotated in the first direction γ, the rotary member 92 is rotated around the central axis C1. This rotation enables cutting of the living tissue with the blade 98 of the working portion 96.

In this operation, because the interlocking member 212 is pushed up in the second direction ζ around the rotating shaft 214 with the driving knob 182 toward the inside of the operation portion main body 82, the fitting portion 216 of the interlocking member 212 is in the state of not being fitted into the fitting receiving portion 202 of the operation portion main body 82. For this reason, the opening/closing knob 84 is rotatable in the second direction β. When the opening/closing knob 84 is rotated in the second direction β, the driving knob 182 abutting against the opening/closing knob 84 is also rotated in the second direction δ. Then, the fitting portion 216 of the interlocking member 212 interlocking with the opening/closing knob 84 is separated from the fitting receiving portion 202 of the support portion 204 of the operation portion main body 82.

Accordingly, the blade 98 of the working portion 96 is moved from the second guide portion 104 to the first guide portion 102 and extracted from the living tissue, and the second holding portion 74 is opened with respect to the first holding portion 72. Specifically, the rotary member 92 is operated, and the treatment portion 42 is also operated.

The first and second holding portions 72 and 74 in the opened state are moved forward with respect to the living tissue, and the opening/closing knob 84 is brought close to the other end 82b of the operation portion main body 82, to close the first and second holding portions 72 and 74. Then, the pedal 16a of the foot switch 16 is pressed, to treat the living tissue with thermal energy. Thereafter, the driving knob 182 is operated, to cut the living tissue with the blade 98 of the working portion 96 of the rotary member 92. Thereafter, the opening/closing knob 84 is rotated toward the second direction β, to retract the working portion 96 from the second guide portion 104 into the first guide portion 102. Repeating such work in order enables successively conjugating and cutting of not only the living tissue between the holding surfaces 72a and 74a but also the living tissue continuously positioned ahead.

The following is a schematic explanation of operations of the operation portion 46 described above. First, the opening/closing knob 84 rotatable in the first and second directions α and β with respect to the operation portion main body 82 held by the operator is rotated in the first direction α, to operate the treatment portion 42 to cause the treatment portion 42 to exert the function of the treatment portion 42 on the living tissue. Next, the interlocking member 212 that interlocks with the opening/closing knob 84 and is rotatable in the third and fourth directions ε and ζ together with rotation of the opening/closing knob 84 is properly rotated and engaged with the operation portion main body 82, to operate the treatment portion 42 to maintain the state of exerting the function on the living tissue. In the state where the operated state of the treatment portion 42 is maintained, the driving knob 182 rotatable in the fifth and sixth directions γ and δ is rotated in the fifth direction γ, to rotate the rotary member 92 around the central axis C1 and cause the rotary member 92 to exert the function of the rotary member 92 on the living tissue. With rotation of the driving knob 182 in the fifth direction γ, the interlocking member 212 is rotated in the fourth direction ζ, to disengage the interlocking member 212 from the operation portion main body 82. Lastly, with rotation of the opening/closing knob 84 in the second direction β, the exertion of the function of the treatment portion 42 is stopped, and the driving knob 182 is rotated in the sixth direction δ, to stop the exertion of the function of the rotary member 92.

As described above, the present embodiment achieves the following.

The present embodiment enables an operation of rotating the opening/closing knob 84 that is rotatably supported by the operation portion main body 82 in the first direction α, holding the living tissue between the first and second holding surfaces 72 and 74, thereafter pressing the pedal 16a of the foot switch 16, to perform treatment of adding thermal energy to the living tissue held between the energy output portions 44 and 54. By operating the driving knob 182 in this state, the present embodiment enables removal of the state in which the interlocking member 212 interlocking with the opening/closing knob 84 is engaged with the operation portion main body 82, and cutting of the living tissue with the edge portion 96a of the working portion 96.

Accordingly, the present embodiment enables the operator to perform a series (one cycle) of operations of holding the living tissue between the holding portions 72 and 74, outputting energy from the energy output portions 44 and 54 to the held living tissue, treating the living tissue (treating with the treatment portion 42), cutting the treated living tissue with the edge portion 96a of the working portion 96 of the rotary member 92, and retracting the edge portion 96a of the working portion 96 of the rotary member 92 into the first guide portion 102 of the first holding portion 72 while removing the holding of the living tissue between the holding portions 72 and 74, only by operations of the opening/closing knob 84 and the driving knob 182 with one hand of the operator. Specifically, the present embodiment enables treatment without excessive operations.

In addition, because the interlocking member 212 in the state of being fitted into the operation portion main body 82 can be released from the fitting by an operation of the driving knob 182, the present embodiment enables the interlocking member 212 to interlock with not only the opening/closing knob 84, but also the driving knob 184. This structure removes a troublesome operation of, for example, moving the driving knob 182 forward to cut the living tissue, thereafter moving the driving knob 182 backward, and removing the state in which the opening/closing knob 84 is fitted into the operation portion main body 82. This structure enables the treatment device to efficiently perform a series of works including treatment of the living tissue using energy and cutting of the living tissue, and markedly improves the efficiency of the work in treating and cutting the living tissue positioned in front of the treated and cut living tissue in the same manner.

Both or one of the projections 190 and 212a are not always necessary, as long as the driving knob 182 is caused to abut against the interlocking member 212 earlier than the timing at which the driving knob 182 abuts against the opening/closing knob 84, when the driving knob 182 is rotated in the first direction γ in the state in which the interlocking member 212 is fitted into the operation portion main body 82.

Although the present embodiment illustrates the example of using the bevel gear 170, a miter gear, which is a type of bevel gear, may suitably be used.

The following is an explanation of a fourth embodiment with reference to FIG. 13A and FIG. 13B. The present embodiment is a modification of the first to third embodiments. The same members or members having the same function as the members explained in the first to third embodiments are denoted by the same respective reference numerals, and detailed explanation thereof is omitted.

The present embodiment illustrates a modification of the mechanism to operate the rotary member 92.

As illustrated in FIG. 13B, an actuator 252 such as a rotary motor is disposed inside the operation portion main body 82 of the operation portion 46. As illustrated in FIG. 13A and FIG. 13B, a switch (rotation operation portion) 254 to operate the rotary member 92 with the actuator 252 is disposed outside the operation portion main body 82.

As illustrated in FIG. 13A, the switch 254 includes, for example, a lever 256. In the present embodiment, the lever 256 can be switched between two modes. The first mode is a stop position to stop the operation of the actuator 252, that is, an initial return position to move the blade 98 of the working portion 96 of the rotary member 92 to the inside of the first guide portion 102. The second mode is a cut position to operate the actuator 252, move the blade 98 of the working portion 96 of the rotary member 92 from the first guide portion 102 to the second guide portion 104, and cut the living tissue.

With this structure, when the position of the lever 256 is switched from the first mode to the second mode, the blade 98 of the working portion 96 of the rotary member 92 is moved from the first guide portion 102 to the second guide portion 104. Thereafter, when the position of the lever 256 is switched from the second mode to the first mode, the blade 98 of the working portion 96 of the rotary member 92 is moved from the second guide portion 104 to the first guide portion 102.

The actuator 252 and the switch 254 are preferably connected to the control unit 22 of the controller 14. This structure enables proper control of the actuator 252. For example, the actuator 252 is prevented from operating even when the lever 256 is moved to the cut position when the energy is output from the energy output circuit 24.

Although the present embodiment illustrates the example in which the actuator 252 is disposed in the operation portion main body 82, the actuator 252 may suitably be disposed, for example, inside the insertion portion 44.

Figure 14:
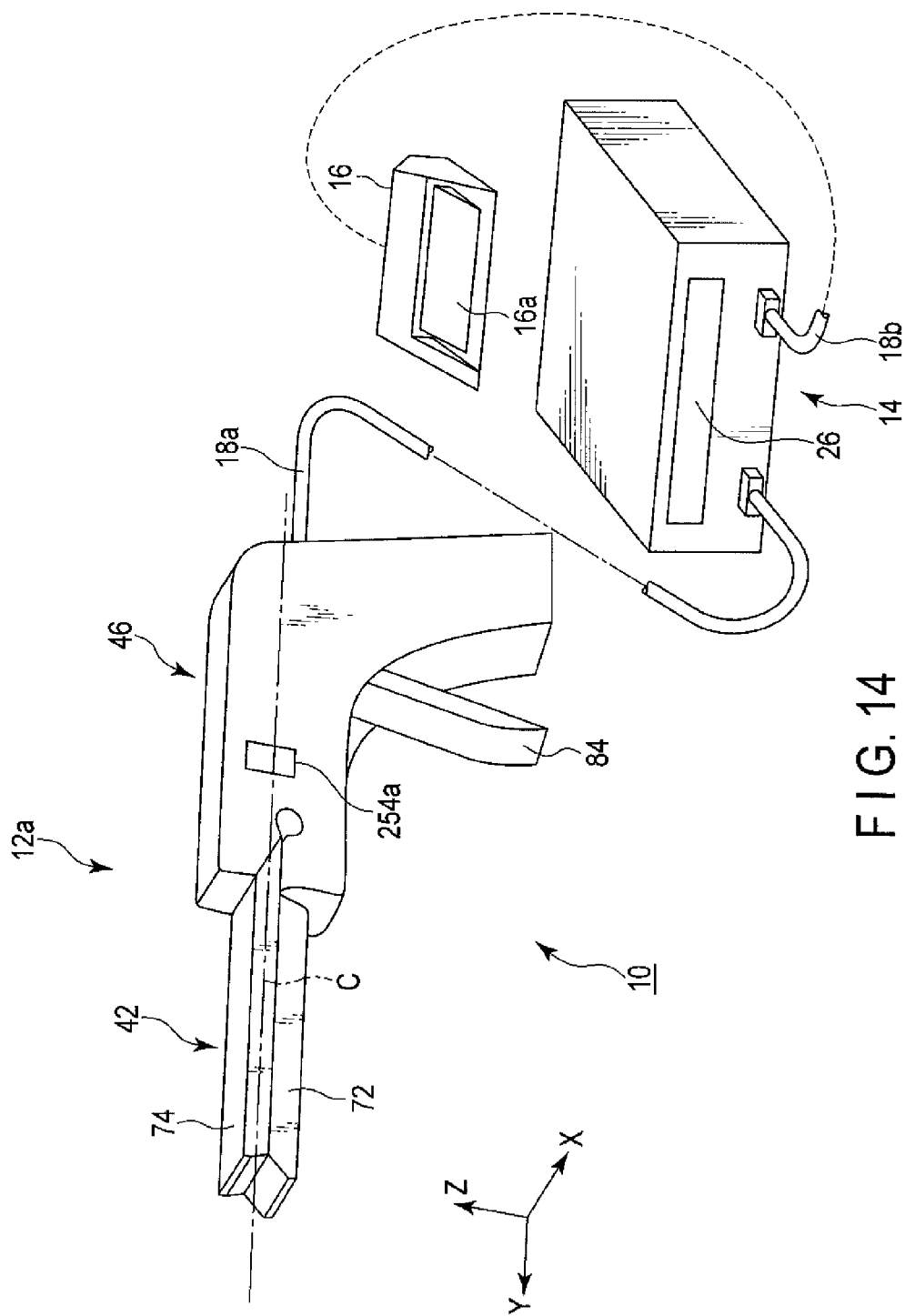
FIG. 14 is a schematic perspective view illustrating a treatment system according to a fifth embodiment.

The following is an explanation of a fifth embodiment with reference to FIG. 14. The present embodiment is a modification of the first to fourth embodiments. The same members or members having the same function as the members explained in the first to fourth embodiments are denoted by the same respective reference numerals, and detailed explanation thereof is omitted.

Although the treatment devices 12 according to the first to fourth embodiments described above have been explained with the examples in which the insertion portion 44 is disposed between the treatment portion 42 and the operation portion 46, the insertion portion 46 is not indispensable, as in a treatment device 12a illustrated in FIG. 14. A switch 254a, when pressed, causes the actuator 252 (see FIG. 13B) to operate, and causes the edge portion 96a of the working portion 96 of the rotary member 92 to move toward the second guide groove 104. When the switch 254a is released from the press, the actuator 254 is operated to move the edge portion 96a of the working portion 96 of the rotary member 92 toward the first guide groove 102.

The following is an explanation of a sixth embodiment with reference to FIG. 15A to FIG. 15C. The present embodiment is a modification of the first to fifth embodiments. The same members or members having the same function as the members explained in the first to fifth embodiments are denoted by the same respective reference numerals, and detailed explanation thereof is omitted.

The treatment portion opening/closing knob 84 of the treatment device 12 according to the sixth embodiment includes a cover 262 that covers the dial 86 (see FIG. 1A), the lever 132 (see FIG. 1B), the switch 254 (see FIG. 13A and FIG. 13B), and/or the switch 254a (see FIG. 14), to prevent the edge portion 96a of the working portion 96 from moving toward the second guide groove 104 (see FIG. 4A to FIG. 4C), before the treatment portion opening/closing knob 84 is brought close to the other end of the operation portion main body 82 and the first holding portion 72 and the second holding portion 74 of the treatment portion 42 are brought close to each other to be closed.

As illustrated in FIG. 15A and FIG. 15B, the cover 262 is formed to extend from the knob 84 along an external peripheral surface of the operation portion main body 82. The cover 262 is capable of covering the dial 86 (the lever 132, or the switch 254 or 254a may be covered instead of the dial 86) to make the dial inoperable, in the state where the knob 84 is brought apart from the other end 82b of the operation portion main body 82 to bring the first holding portion 72 and the second holding portion 74 of the treatment portion 42 apart from each other to open them. In addition, as illustrated in FIG. 15C, the cover 262 is capable of exposing the dial 86 (the lever 132, or the switch 254 or 254a may be exposed instead of the dial 86) to make the dial operable, in the state where the knob 84 is brought close to the other end 82b of the operation portion main body 82 to bring the first holding portion 72 and the second holding portion 74 of the treatment portion 42 close to each other to close them. The cover 262 is formed to move from the state illustrated in FIG. 15A to the state illustrated in FIG. 15C along the external surface of the operation portion main body 82, to be prevented from interfering with the operation portion main body 82 in response to rotation (bringing the knob 84 close to and apart from the other end 82b of the operation portion main body 82) of the knob 84.

Specifically, the opening/closing knob (opening/closing operation portion) 84 is configured to expose at least part of the dial 86, the lever 132, and/or the switches 254 and 254a serving as the rotation operation portion, in the state where the first and the second holding portions 72 and 74 are brought close to each other and closed. The opening/closing knob (opening/closing operation portion) 84 is configured to cover the dial 86, the lever 132, and/or the switches 254 and 254a serving as the rotation operation portion, in the state where the first and the second holding portions 72 and 74 are brought apart from each other and opened.

Although the cover 262 is illustrated to protect the left side surface and the right side surface of the operation portion main body 82 as in FIG. 15B, the cover 262 may suitably be formed on only the left side surface when the dial 86 (the lever 132, or the switch 254 or 254a may be disposed instead of the dial 86) is disposed on the left side surface of the operation portion main body 82, or may suitably be formed on only the right side surface when the dial 86 is formed on the right side surface.

The details of the structure illustrated in FIG. 15A to FIG. 15C will be explained hereinafter. The cover 262 that extends from the knob 84 extends along the external surface of the operation portion main body 82, to the position in which the dial 86 (the lever 132, or the switch 254 or 254*a* may be disposed instead of the dial 86) is disposed. In the state illustrated in FIG. 15A, the cover 262 may have various structures to prevent the operator from operating the dial 86 (which may be the lever 132, or the switch 254 or 254*a*, instead of the dial 86). For example, the cover 262 may be configured to extend along the dial 86, the lever 132, the switch 254, and/or switch 254*a*, to have a width to cover the whole dial 86 (which may be the lever 132, or the switch 254 or 254*a*, instead of the dial 86). The cover 262 may be configured to cover part of the dial 86 (which may be the lever 132, or the switch 254 or 254*a*, instead of the dial 86), as long as the cover 262 prevents the dial 86 (which may be the lever 132, or the switch 254 or 254*a*, instead of the dial 86) from being operated.

The operation portion main body 82 can define a position in which the opening/closing knob 84 is most apart from the other end 82*b* (see FIG. 15A) with an abutting portion 264*a*, and define a position in which the opening/closing knob 84 is closest to the other end 82*b* (see FIG. 15C) with an abutting portion 264*b*.

With the above structure, as illustrated in FIG. 15C, the operator cannot operate the dial 86 (which may be the lever 132, or the switch 254 or 254*a*, instead of the dial 86), unless the operator brings the knob 84 close to the other end 82*b* of the operation portion main body 82 to bring the first holding portion 72 and the second holding portion 74 of the treatment portion 42 to be closed. For this reason, the edge portion 96*a* of the working portion 96 cannot be moved toward the second guide groove 104, in the state where the operator brings the opening/closing knob 84 apart from the other end 82*b* of the operation portion main body 82. This structure prevents the first holding portion 72 and the second holding portion 74 from being opened or closed, in the state where the first holding portion 72 and the second holding portion 74 are brought apart from each other and the edge portion 96*a* of the working portion 96 is exposed from the holding surface 72*a* of the first holding portion 72.

The following is an explanation of a seventh embodiment with reference to FIG. 16A and FIG. 16B. The present embodiment is a modification of the first to sixth embodiments. The same members or members having the same function as the members explained in the first to sixth embodiments are denoted by the same respective reference numerals, and detailed explanation thereof is omitted.

The present embodiment is, in particular, a modification of the sixth embodiment. The treatment portion opening/closing knob 84 of the treatment device 12 according to the seventh embodiment includes a cover 266 that covers the driving knob 182 (see FIG. 11A, and FIG. 12A to FIG. 12C), to prevent the edge portion 96*a* of the working portion 96 from moving toward the second guide groove 104 (see FIG. 4A to FIG. 4C), before the treatment portion opening/closing knob 84 is brought close to the other end of the operation portion main body 82 and the first holding portion 72 and the second holding portion 74 of the treatment portion 42 are brought close to each other to be closed.

As illustrated in FIG. 16A, the cover 266 is formed to extend from the knob 84 forward. The cover 266 is capable of covering the knob 182 to make the knob inoperable, in the state where the knob 84 is brought apart from the other end 82*b* of the operation portion main body 82 to bring the first holding portion 72 and the second holding portion 74 of the treatment portion 42 apart from each other to be opened. In addition, as illustrated in FIG. 16B, the cover 266 is capable of exposing the knob 84 to make the knob operable, in the state where the knob 84 is brought close to the other end 82*b* of the operation portion main body 82 to bring the first holding portion 72 and the second holding portion 74 of the treatment portion 42 close to each other to be closed. The cover 266 is formed to move from the state illustrated in FIG. 16A to the state illustrated in FIG. 16B along the external surface of the operation portion main body 82, to be prevented from interfering with the operation portion main body 82 in response to rotation (bringing the knob 84 close to and apart from the other end 82*b* of the operation portion main body 82) of the knob 84.

Specifically, the opening/closing knob (opening/closing operation portion) 84 is configured to cover at least part of the driving knob 182 serving as the rotation operation portion, in the state where the first and the second holding portions 72 and 74 are brought close to each other and closed. The opening/closing knob (opening/closing operation portion) 84 is configured to expose the driving knob 182 serving as the rotation operation portion, in the state where the first and the second holding portions 72 and 74 are brought apart from each other and opened.

Although the cover 266 is illustrated to cover the front side of the driving knob 182 as in FIG. 16A, the cover 266 may suitably be formed to cover the left side surface and the right side surface, as well as the front side, to prevent the operator from touching it.

The driving knob 182 is attached to the operation portion main body 82 such that the driving knob 182 is disposed on the distal end side beyond the attaching position of the opening/closing knob 84 to the operation portion main body 82. The driving knob 182 is configured to be rotated or pushed from the distal end side toward the proximal end side of the operation portion main body 82. The cover 266 extends from the knob 84 to the distal end side of the operation portion main body 82, and extends to the position where the driving knob 182 is placed. In the state illustrated in FIG. 16A, the cover 266 may have various structures to prevent the operator from operating the driving knob 182. For example, the cover 266 may be configured to extend along the driving knob 182, to have a width to cover the whole driving knob 182. The cover 266 may be configured to cover part of the driving knob 182, as long as the cover 266 prevents the driving knob 182 from being operated.

With the above structure, as illustrated in FIG. 16B, the operator cannot operate the driving knob 182, unless the operator brings the knob 84 close to the other end 82*b* of the operation portion main body 82 to bring the first holding portion 72 and the second holding portion 74 of the treatment portion 42 to be closed. For this reason, the edge portion 96*a* of the working portion 96 cannot be moved toward the second guide groove 104, in the state where the operator brings the opening/closing knob 84 apart from the other end 82*b* of the operation portion main body 82. This structure prevents the first holding portion 72 and the second holding portion 74 from being opened or closed, in the state where the first holding portion 72 and the second holding portion 74 are brought apart from each other and the edge portion 96*a* of the working portion 96 is exposed from the holding surface 72*a* of the first holding portion 72.

Although the details thereof are not illustrated, the treatment portion opening/closing knob 84 may suitably be provided with both the cover 262 explained in the sixth embodiment illustrated in FIG. 15A to FIG. 15C and the cover 266 explained in the seventh embodiment illustrated in FIG. 16A and FIG. 16B.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device to treat a living tissue, comprising:
   first and second holders including a longitudinal axis and including respective holding surfaces configured to be spaced apart from each other in an open configuration and to move close to each other in a closed configuration that is capable of holding the living tissue therebetween, an opening/closing direction orthogonal to or substantially orthogonal to the longitudinal axis being defined by an open and closed position of the holding surfaces;
   a rotary shaft configured to rotate about a central axis spaced apart and parallel or substantially parallel with the longitudinal axis, the rotary shaft including a blade which comprises an edge as a cutter pointed in a periaxial direction of the central axis and spaced apart from the central axis, the rotary shaft being configured to move the edge along the periaxial direction of the central axis from the first holder to the second holder by a rotation of the rotary shaft;
   a first guide including a first opening provided in the holding surface of the first holder, the first guide being configured to contain the edge to prevent the edge from projecting from the holding surface of the first holder through the first opening, and configured to guide the edge toward the second holder through the holding surface of the first holder; and
   a second guide including a second opening provided in the holding surface of the second holder, and configured to guide the edge,
   wherein the edge is rotated about the central axis along the periaxial direction from the first guide to the second guide through the first opening of the first guide and the second opening of the second guide, and is configured to cut the living tissue along the longitudinal axis between the holding surface of the first holder and the holding surface of the second holder when the rotary shaft is rotated around the central axis.

2. The treatment device according to claim 1, wherein:
   a width direction in a direction orthogonal to or substantially orthogonal to the longitudinal axis is defined by the holding surfaces of the first and second holders,
   each of the holding surfaces of the first and second holders has a first end and a second end in the width direction,
   the first opening of the first guide is provided between the first end of the first holder and the second end of the first holder in the width direction, the edge being received by the first guide through the first opening, and
   the second opening of the second guide is provided between the first end of the second holder and the second end of the second holder in the width direction and is opposed to the first opening, the edge being received by the second guide through the second opening by the rotation of the rotary shaft.

3. The treatment device according to claim 2, wherein:
   the first guide includes a curved or inclined first recessed groove continuous with the first opening and extending from the holding surface of the first holder toward a back surface of the first holder, and
   the second guide includes a curved or inclined second recessed groove continuous with the second opening and extending from the holding surface of the second holder toward a back surface of the second holder.

4. The treatment device according to claim 3, wherein:
   the first recessed groove extends toward one of the first end and the second end of the first holder in the width direction as the first recessed groove approaches the back surface of the first holder, and
   as the second recessed groove approaches to the back surface of the second holder, the second recessed groove extends toward a same end of the second holder as the first recessed groove extends toward in the first holder.

5. The treatment device according to claim 1, wherein the edge is parallel with the central axis throughout its rotation about the central axis.

6. The treatment device according to claim 1, wherein:
   the edge includes a distal end portion and a proximal end portion along the longitudinal axis, and
   the distal end portion is configured to project from the holding surface of the first holder before the proximal end portion when the rotary shaft is rotated around the central axis.

7. The treatment device according to claim 1, wherein:
   the edge includes a distal end portion and a proximal end portion along the longitudinal axis, and
   the proximal end portion is configured to project from the holding surface of the first holder before the distal end portion when the rotary shaft is rotated around the central axis.

8. The treatment device according to claim 1, wherein:
   the edge includes a distal end portion and a proximal end portion along the longitudinal axis, and a central portion located between the distal end portion and the proximal end portion, and
   at least one of the distal end portion and the proximal end portion is configured to project from the holding surface of the first holder before the central portion when the rotary shaft is rotated around the central axis.

9. The treatment device according to claim 1, wherein:
   the edge includes a distal end portion and a proximal end portion along the longitudinal axis, and a central portion located between the distal end portion and the proximal end portion, and
   the central portion is configured to project from the holding surface of the first holder before at least one of the distal end portion and the proximal end portion when the rotary shaft is rotated around the central axis.

10. The treatment device according to claim 1, further comprising an operation main body including a movable handle which is configured to open and close the first and second holders by an operation of the movable handle.

11. The treatment device according to claim 10, further comprising:
    a rotation operator which is configured to rotate the rotary shaft around the central axis to project the edge from each of the holding surfaces of the first and second holders,
    wherein the movable handle is configured to cover at least part of the rotation operator in a state where the first and second holders are brought apart from each other and opened.

12. The treatment device according to claim 10, further comprising:

a rotation operator which is configured to rotate the rotary shaft around the central axis to project the edge from the holding surface of the first holder; and a cover on the movable handle configured to expose the rotation operator in a state where the first and second holders are brought close to each other and closed.

13. The treatment device according to claim 10, further comprising:

a rotation operator which rotates the rotary shaft around the central axis to project the edge from the holding surface of the first holder, wherein the rotation operator includes at least one of a dial and a lever projecting outside the operation main body which rotates the rotary shaft around the central axis when adapted to be operated by the user.

14. The treatment device according to claim 1, further comprising:

a rotation operator which is configured to rotate the rotary shaft around the central axis to project the edge from the holding surface of the first holder, wherein the rotation operator includes a gear which is adapted to be operated by the user and which transmits motive power to rotate the rotary shaft.

15. The treatment device according to claim 14, wherein the rotation operator includes a knob adapted to be operated by the user to operate the gear.

16. The treatment device according to claim 1, further comprising:

an operation main body including:

a movable handle which is configured to open and close the first and second holders by an operation of the movable handle;

an actuator which is configured to rotate the rotary shaft around the central axis; and a switch to operate the actuator.

17. The treatment device according to claim 1, wherein the rotary shaft comprises a cylindrical portion.

18. The treatment device according to claim 1, wherein the rotary shaft comprises a half pipe portion.

* * * * *